United States Patent
Levin et al.

(10) Patent No.: US 12,208,161 B2
(45) Date of Patent: Jan. 28, 2025

(54) DEVICE FOR CUTTING AN ANIMAL TREAT COMPOSITION

(71) Applicant: JMN Technologies LLC, Omaha, NE (US)

(72) Inventors: Mark A. Levin, Omaha, NE (US); Joanne N. Levin, Omaha, NE (US)

(73) Assignee: JMN Technologies LLC, Omaha, NE (US)

( * ) Notice: Subject to any disclaimer, the term of this patent is extended or adjusted under 35 U.S.C. 154(b) by 358 days.

(21) Appl. No.: 17/665,372

(22) Filed: Feb. 4, 2022

(65) Prior Publication Data

US 2022/0265548 A1 Aug. 25, 2022

Related U.S. Application Data

(62) Division of application No. 16/892,220, filed on Jun. 3, 2020, now Pat. No. 11,654,107.

(60) Provisional application No. 62/856,594, filed on Jun. 3, 2019.

(51) Int. Cl.
| | |
|---|---|
| A61K 9/00 | (2006.01) |
| A23K 10/20 | (2016.01) |
| A23K 10/33 | (2016.01) |
| A23K 20/163 | (2016.01) |
| A23K 40/25 | (2016.01) |
| A61K 9/20 | (2006.01) |

(52) U.S. Cl.
CPC ............ *A61K 9/0056* (2013.01); *A23K 10/20* (2016.05); *A23K 10/33* (2016.05); *A23K 20/163* (2016.05); *A23K 40/25* (2016.05); *A61K 9/2018* (2013.01); *A61K 9/2054* (2013.01); *A61K 9/2059* (2013.01); *A61K 9/2063* (2013.01); *A61K 9/2068* (2013.01); *A61K 9/2095* (2013.01); *A61K 9/2072* (2013.01)

(58) Field of Classification Search
None
See application file for complete search history.

(56) References Cited

U.S. PATENT DOCUMENTS

| | | |
|---|---|---|
| 2,090,095 A | 8/1937 | Bainbridge |
| 3,059,400 A | 10/1962 | Plummer et al. |
| 5,747,063 A | 5/1998 | Languet et al. |
| 5,853,757 A | 12/1998 | Durand et al. |
| 8,501,218 B2 | 8/2013 | Hurwitz |
| 2004/0247665 A1 | 12/2004 | Smith et al. |
| 2005/0255148 A1 | 11/2005 | Puma |
| 2007/0298077 A1 | 12/2007 | Jones |
| 2009/0148589 A1 | 6/2009 | Fox et al. |
| 2009/0297569 A1 | 12/2009 | Hurwitz |
| 2011/0076363 A1 | 3/2011 | Niehues |
| 2011/0256208 A1 | 10/2011 | Ling |
| 2013/0171204 A1 | 7/2013 | DuBourdieu et al. |
| 2015/0313185 A1 | 11/2015 | Barnvos et al. |
| 2017/0042805 A1 | 2/2017 | Goldberg |
| 2020/0375893 A1 | 12/2020 | Levin et al. |

FOREIGN PATENT DOCUMENTS

WO 2004043427 A1 5/2004

OTHER PUBLICATIONS

"Eptech Food Processing Systems [website]," 6 pages, Jun. 2021, Web page retrieved from <https://www.eptech.co.za/11-cutting/28-fam-ts-1d> on Oct. 15, 2020.
"Eptech Food Processing Systems [website]," 9 pages, Jun. 2021, Web page retrieved from https://www.eptech.co.za/11-cutting/51-kronen-gs-20> on Oct. 15, 2020.
English translation (from Google Patents) of Maloisel WO 2004043427 A1 (pp. 1-8). (Year: 2004).

*Primary Examiner* — Aradhana Sasan
(74) *Attorney, Agent, or Firm* — POLSINELLI PC

(57) ABSTRACT

An animal treat composition for the oral administration of a medication to an animal is disclosed. The animal treat composition comprises an adhesive portion core and an outer portion. The adhesive portion adheres to oral medication inserted into the adhesive core of the treat for administration of the medication to an animal.

18 Claims, 11 Drawing Sheets

DEVICE FOR CUTTING AN ANIMAL TREAT COMPOSITION

CROSS-REFERENCE TO RELATED APPLICATIONS

This application is a Divisional of U.S. application Ser. No. 16/892,220, filed Jun. 3, 2020, which claims priority from Provisional Application No. 62/856,594, filed Jun. 3, 2019, the contents of which are hereby incorporated by reference in their entirety.

FIELD OF THE INVENTION

The present disclosure provides an animal treat composition for the oral administration of a medication.

BACKGROUND OF THE INVENTION

In animal medicine, oral administration of a medication is often preferred over other routes. For instance, the oral route requires less specialized training than administration of a medication by the intravenous route, thus making it suitable for pet owners to administer a medication without veterinary assistance. However, oral administration of a medication is not without its challenges. When an animal rejects an oral medication, the animal may not receive the complete course of therapy, which results in poor outcomes for the treatment. Oral medications are often rejected by animals because of the taste, smell, and texture of the medication, all of which an animal may find unpalatable.

Earlier attempts at formulating pilling treats have been unable to successfully prevent detachment of the medication from the treat when ingested by the animal. Animals can easily detect the medication, separate the medication from treat components, and consume the treat but expel the medication. This is because earlier attempts at formulating treats for oral administration have been unable to successfully prevent detachment of the medication from the treat when ingested by the animal.

To date, no dual-textured treat is known to deliver a sticky center with sufficient adhesive strength to prevent detachment of the medication from the treat when ingested by the animal. In part, this is because formulations of the textures are not stable, equilibrating with each other over time, allowing moisture or fat migration that effects texture, performance, or appearance. Dual-textured treats that do exist, typically comprise a paste-like center portion and chewy, hard, or crunchy outer portion, and do not exist in a format offering a soft adhesive inner portion to allow for the insertion and adhesion to the medication. To provide a soft inner portion, existing formulations include a high amount of fat, which does not provide sufficient adhesive strength to retain the medication. However, a high fat content is not capable of providing sufficient adhesive strength to prevent detachment of the medication. This is partly because, to be sufficiently sticky entails a formulation having a high water content. In dual textured treats, such formulations are not stable, equilibrating with each other over time, allowing moisture or fat migration that affects texture, performance, or appearance. To overcome this problem, existing approaches include maintaining the food articles at frozen temperatures to stop moisture or fat migrations, or applying an edible barrier to stop water and fat migration. In both shelf stable and frozen temperature approaches, barriers such as solid fats, shellac, or blends and complex copolymers of shellac between the crunchy and the chewy regions, have been evaluated. When an edible barrier is used, the barrier tends to deteriorate over time due to the development of microfissures which can be aggravated by repeated temperature cycling. The edible barrier must also be relatively thick in order to assure complete segregation between the dissimilar textures, leading to undesirable palatability. Finally, high fat levels and shellac ingredients are inconsistent with the perception of wholesomeness in food products, even in food products intended for pets.

Existing approaches to improve the textural stability and palatability of dual-textured pet treats with rigid and soft chewing characteristics have not proven successful. Such approaches include maintaining the food articles at frozen temperatures to stop moisture or fat migrations, or applying an edible barrier to stop water and fat migration. In both shelf stable and frozen temperature approaches, barriers such as solid fats, shellac, or blends and complex copolymers of shellac between the crunchy and the chewy regions, have been evaluated. When an edible barrier is used, the edible barrier tends to deteriorate over time due to the development of microfissures which can be aggravated by repeated temperature cycling. The edible barrier must also be relatively thick in order to assure complete segregation between the dissimilar textures, leading to undesirable palatability. Finally, high fat levels and shellac ingredients are inconsistent with the perception of wholesomeness in food products, even in food products intended for pets.

What is needed, therefore, is an animal treat composition with improved adhesive properties so that the animal treat adheres tightly to the oral medication. It is further desirable and another object of the invention to provide a dual-textured animal treat composition that maintains its distinct dissimilar outer and inner textures over an acceptable shelf life.

SUMMARY OF THE INVENTION

One aspect of the present disclosure encompasses an animal treat for delivery of oral medication to an animal. The treat comprises a semi-solid adhesive inner portion surrounded by a semi-rigid outer portion. The adhesive portion comprises from about 5% to about 50% w/w of one or more sugars; a water content of about 15% w/w or more; a starch comprising a high content of amylopectin or a high ratio of amylopectin to amylose; and a fat content of 3% or less w/w. The oral medication can be a tablet, pill, capsule, or soft gel capsule.

The semi-solid adhesive inner portion can have the texture of a firm gel, a paste, or have an elastic texture. The adhesive inner portion and the outer portion can comprise compatible starch contents and water activities. In some aspects, the starch is waxy rice starch, waxy maize starch, waxy potato starch, tapioca starch, potato starch, or combinations thereof; the sugars are glycerin, liquid or dry molasses, honey, sugar, dextrose, liquid or dried starch hydrolysate, or combinations thereof; and the liquid or dried starch hydrolysate is corn syrup, rice syrup, tapioca syrup, propylene glycol, sorbitol, or combinations thereof.

The water content of the adhesive portion can range from about 15% w/w to about 45% w/w; or from about 20% w/w to about 45% w/w. The adhesive portion can comprise about 10% w/w to about 20% w/w glycerin. Further, the adhesive inner portion can comprise about 20% w/w to about 48% w/w sugar.

The water activity of the adhesive portion ranges from about 0.70 to 0.85. Further, the adhesive portion can comprise a fat content of about 1.5% w/w or lower. The animal treat can be acidified to a pH of 5.3 or less, a pH of about 3 or less, a pH ranging from about 4.5 to about 5.5, or a pH ranging from about 4.8 to about 4.9.

In some aspects, the adhesive portion comprises a thickening agent. The thickening agent can be selected from polysaccharides, agar, carrageenan, cassia gum, carboxy methyl cellulose (CMC), gellan gum, guar gum, konjac gum, locust bean gum, methyl cellulose, hydroxy propyl methyl cellulose (HPMC), pectin, starch, glucomannan, galactomannan, xanthan gum, and carrageenan.

Another aspect of the present disclosure encompasses a device for cutting an extruded dual-textured food product. The device comprises a cutting wheel comprising cutting wires strung between an axle and an outer rim, and a means for rotating the cutting wheel about the axle. The dual-textured product comprises an adhesive inner portion.

Yet another aspect of the present disclosure encompasses a method of preparing a dual-textured animal treat. The method comprises providing or having provided a first food material for forming an adhesive portion; providing or having provided a second food material for forming an outer portion; co-extruding the first and second food materials to form a co-extruded stream such that the outer portion at least partially surrounds the adhesive portion, dividing the extrudate into portions to form the food product; and optionally subjecting the first and second food materials to sufficient temperature during extrusion to cook said first and second food material as said material is extruded.

DETAILED DESCRIPTION OF THE INVENTION

Figure 1:
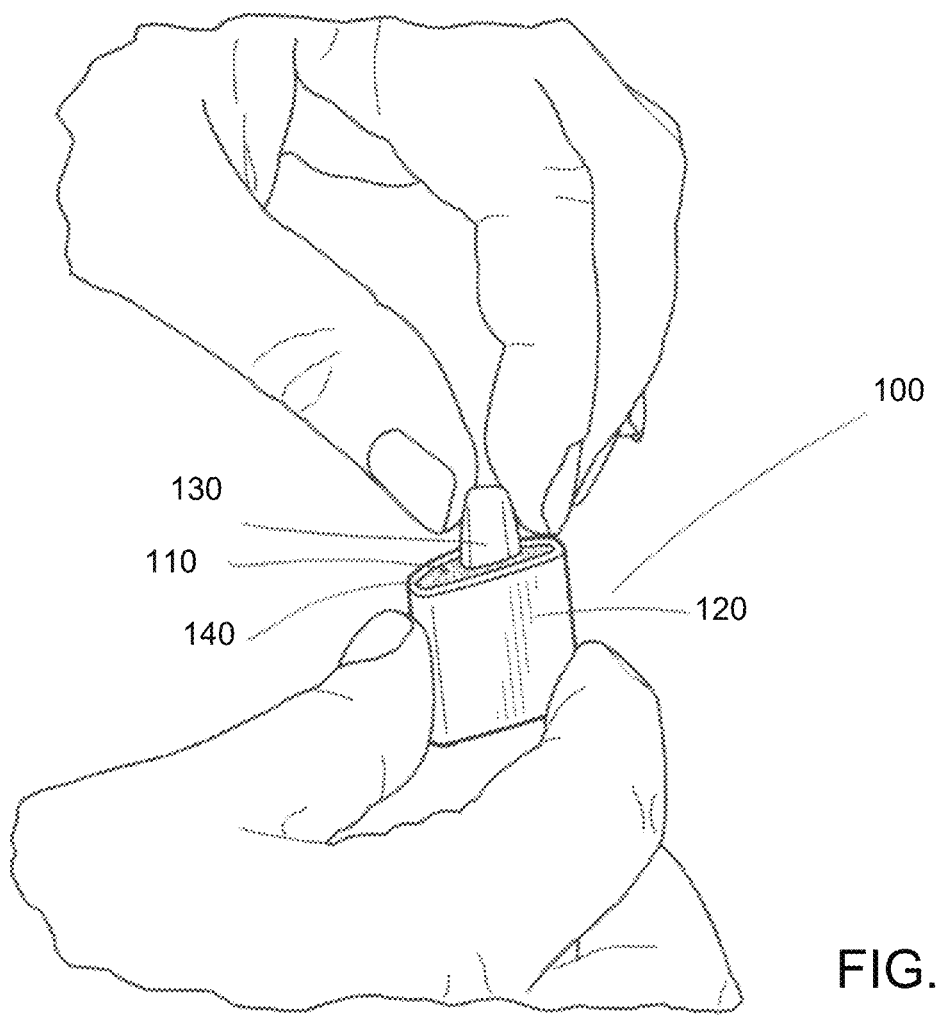
FIG. 1 illustrates an aspect of the method of use where an oral medication is placed into the adhesive portion of the animal treat described by inserting the oral medication into the adhesive portion.

The present invention relates to animal treats (also referred to herein as a "pilling treat") for administering an oral medication to an animal. The treats are dual-textured, comprising an adhesive inner portion, and an outer portion partially surrounding the inner portion. The inner portion has an adhesive strength capable of retaining a medication when administered to an animal and prevent the animal from expelling the medication. Conversely, the outer portion is not sticky, thereby facilitating handling of the treat by a user and preventing the treats from adhering to other treats in the packaging. Surprisingly, despite having inner and outer regions with distinctly dissimilar compositions and textural characteristics, each portion maintains their respective textural integrity for extended periods, e.g., during storage.

The invention is based in part on a number of factors and combinations of factors discovered by the inventor to provide all these beneficial characteristics. For instance, the inventors discovered:

that a starch comprising a high content of amylopectin or high ratio of amylopectin to amylose does not contract or shrink significantly during retrogradation;

that a treat comprising compatible starch contents in the inner and outer portions significantly stabilizes the textural integrity and beneficial characteristics of the inner and outer portions; and that a treat comprising compatible water activities in the inner and outer portions stabilizes the textural integrity and beneficial characteristics of the inner and outer portions.

I. Animal Treat

In one aspect, the present disclosure encompasses composite dual-textured animal treats comprising distinctly dissimilar outer and adhesive inner portions. Both portions of the animal treat are edible and are designed to be palatable to the target animal. The outer portion of the composition partially surrounds the adhesive inner portion. The outer portion is not substantially sticky, and can be sufficiently rigid to facilitate handling of the treat by a user and preventing the treats from adhering to other treats in the packaging. The adhesive portion is sufficiently sticky and malleable to allow insertion of a medication and prevent detachment from the pilling treat even when administered to an animal. The animal treats have an enhanced shelf life, maintaining their textural integrity over extended periods of time. Further, the inner and outer portions can be in direct contact, without the necessity for a separate, distinct barrier between the inner and outer portions to protect the textural integrity of the portions.

A. Dual-Textured Animal Treat.

Dual-textured animal treats of the present disclosure can be of any size and shape suitable for administration to an animal. The treats can have regular shapes such as cubes, cones, discs, or "kisses." Alternatively, an animal treat may be formed into irregular shapes, or shapes that can provide some additional benefits to the animal upon chewing. For instance, the treats can include protrusions to aid in cleaning the animal's teeth. In some aspects, an animal treat composition is generally cylindrical (including square, rectangular, triangular, circular, elliptical, polyhedral, and irregular cylinders). In this aspect, the outer portion surrounds the length of the cylinder to form a tube-like configuration surrounding the adhesive portion.

Figure 2:
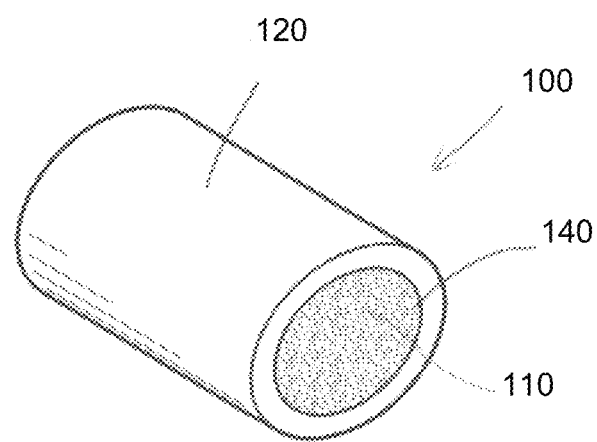
FIG. 2 illustrates an animal treat in accordance with the present disclosure. The figure illustrates the inner adhesive portion and the outer portion of the animal treat.
Figure 3:
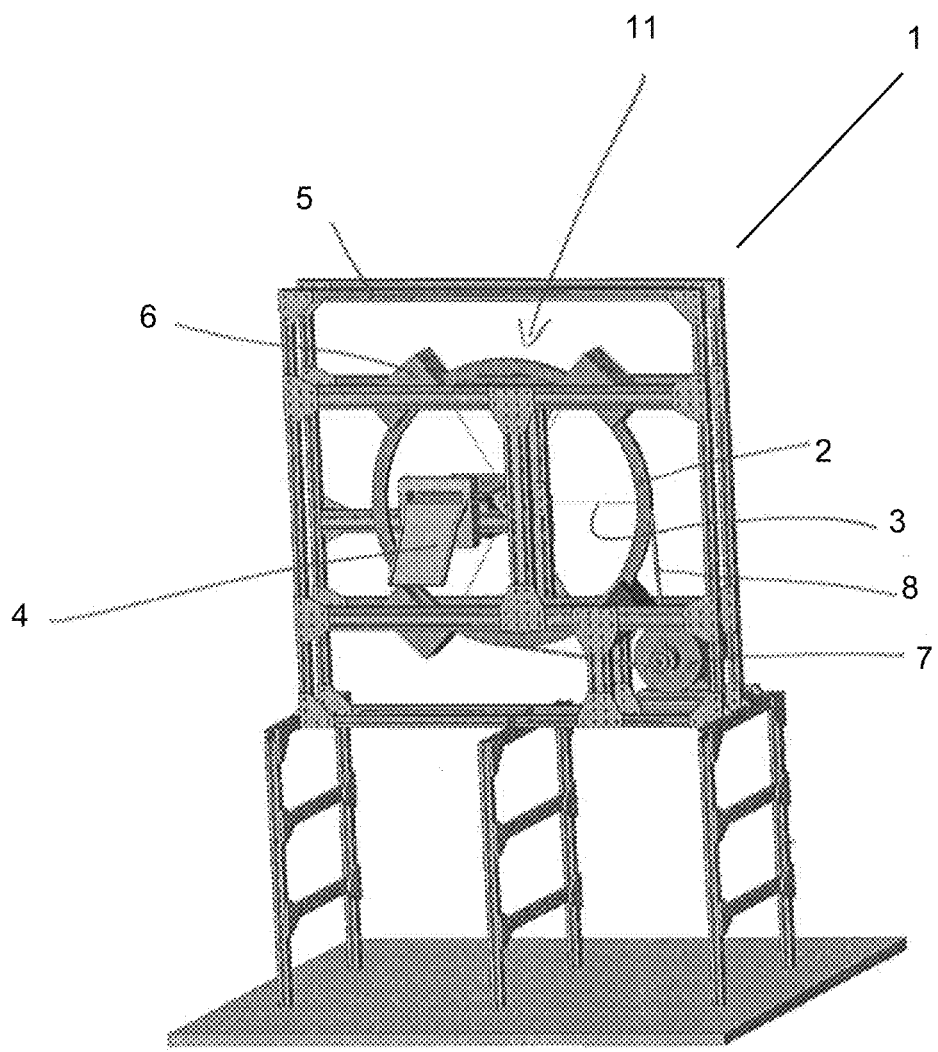
FIG. 3 is a perspective front view of the treat cutting device.
Figure 4:
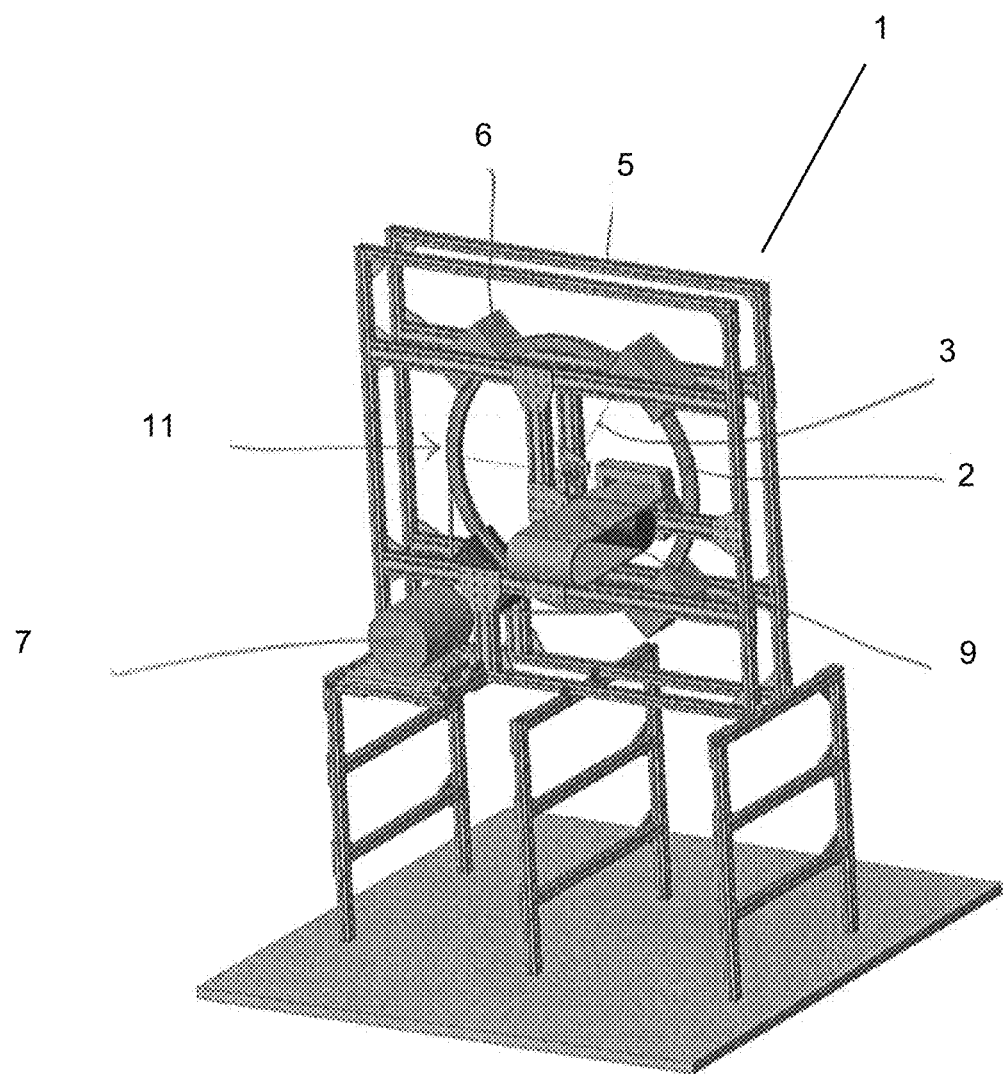
FIG. 4 is a perspective rear view of the treat cutting device.
Figure 5:
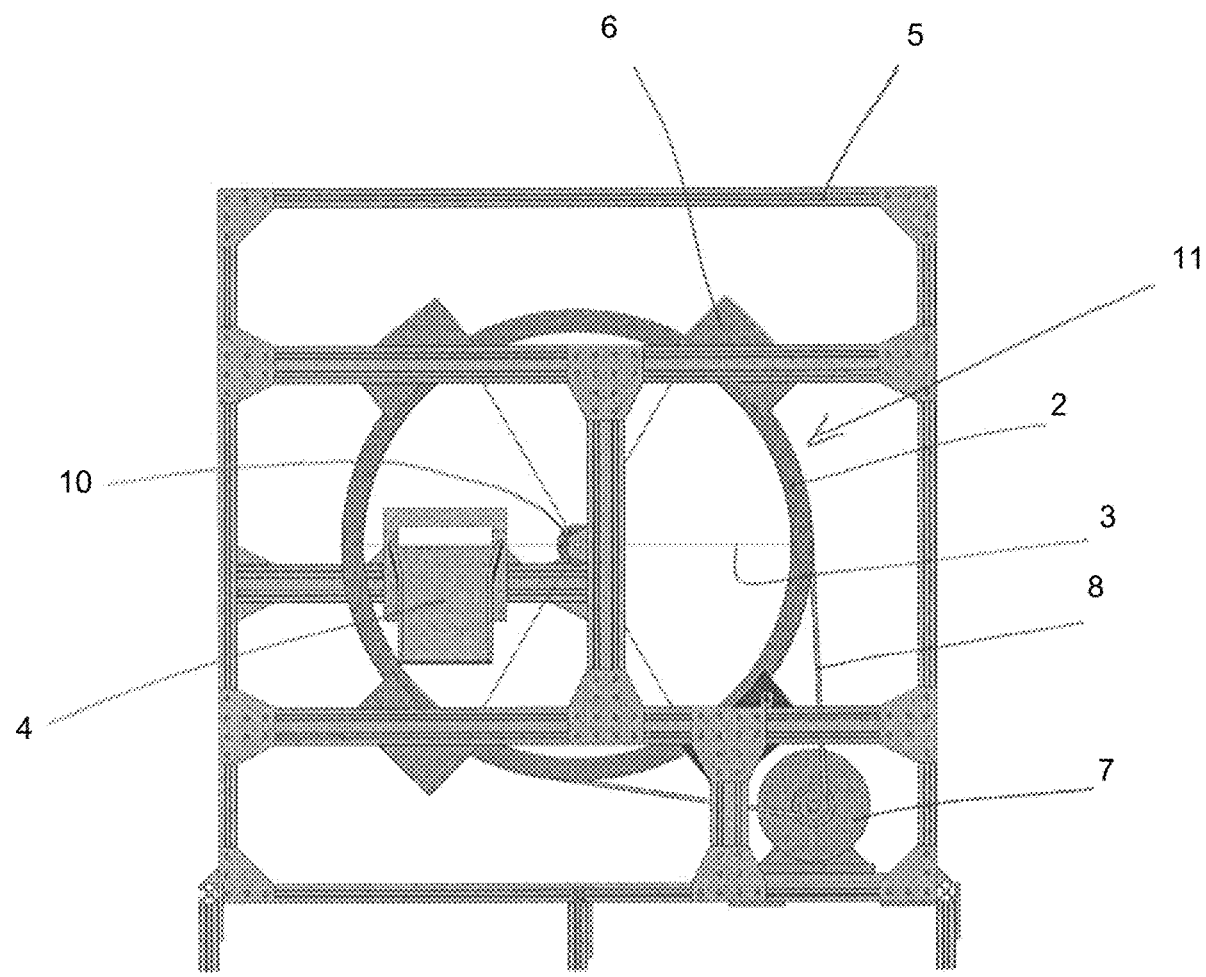
FIG. 5 is a front close-up view of the treat cutting device.
Figure 6:
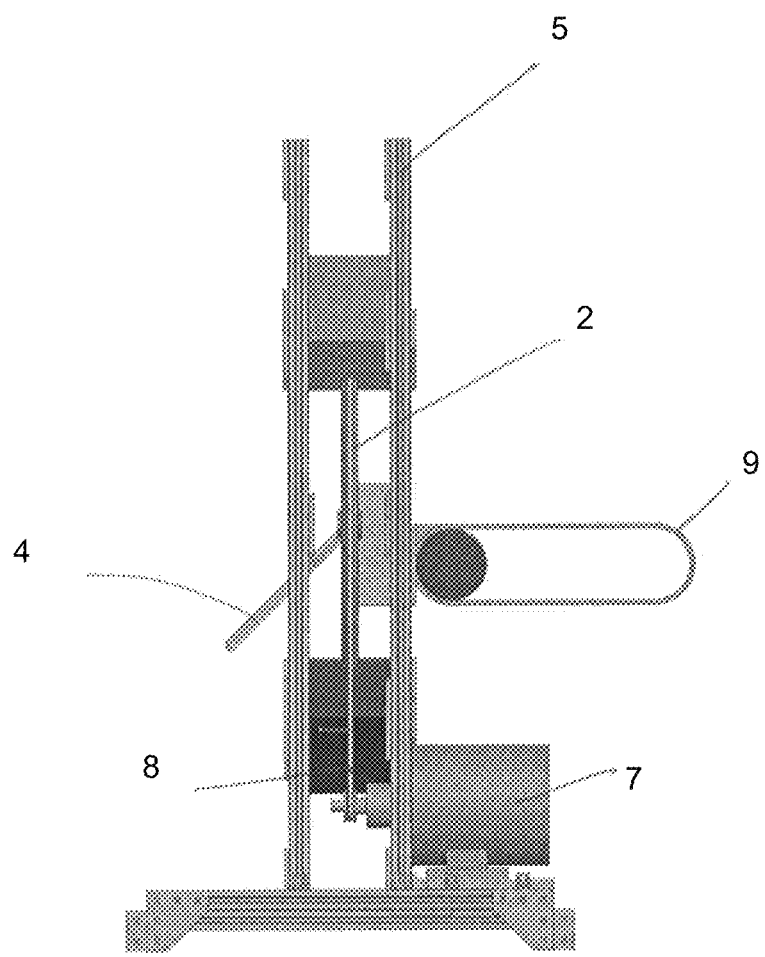
FIG. 6 is a side close-up view of the treat cutting device.
Figure 7:
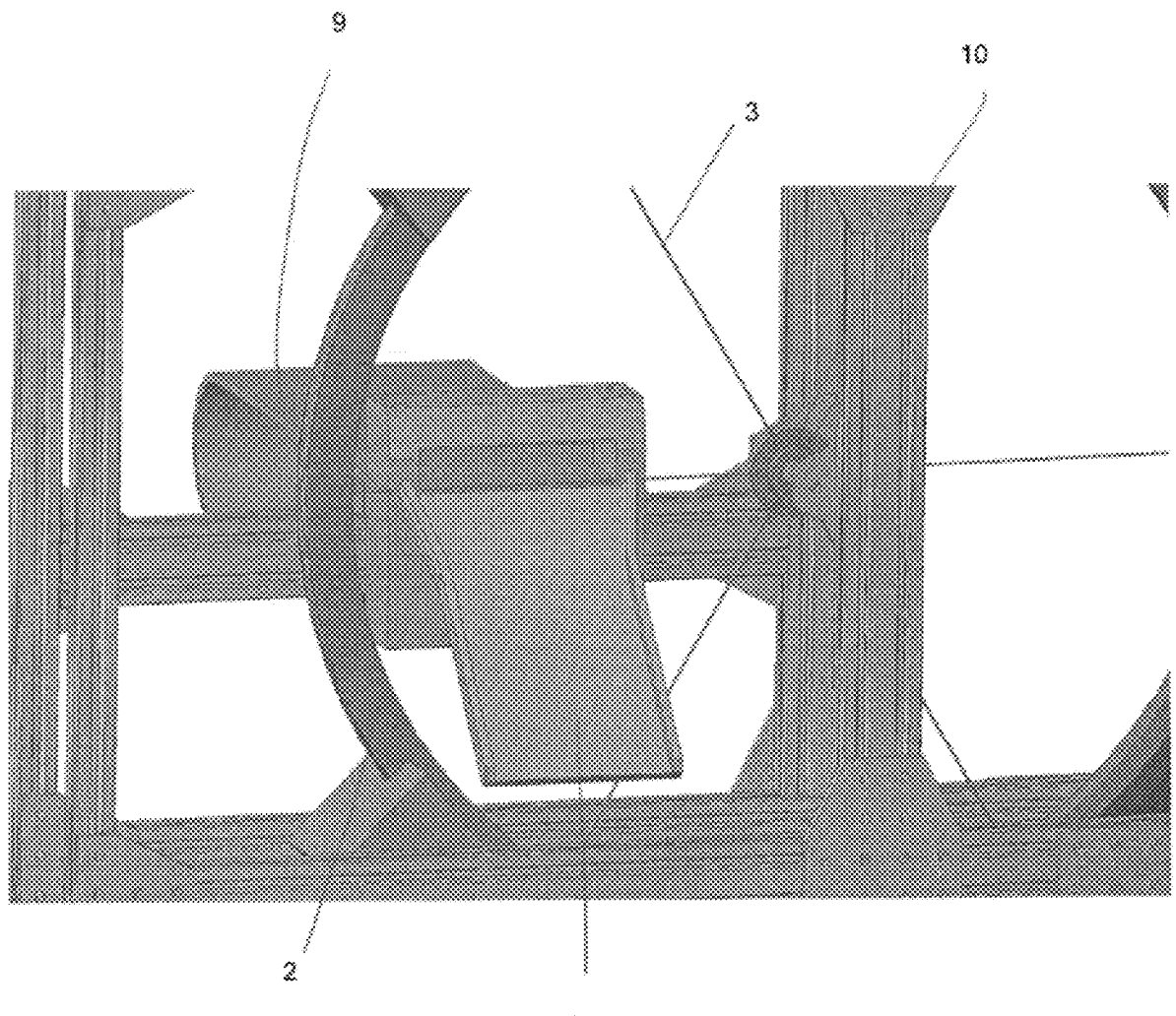
FIG. 7 is a perspective close-up front view showing the cutting wire, the treat chute and the conveyor belt.
Figure 8:
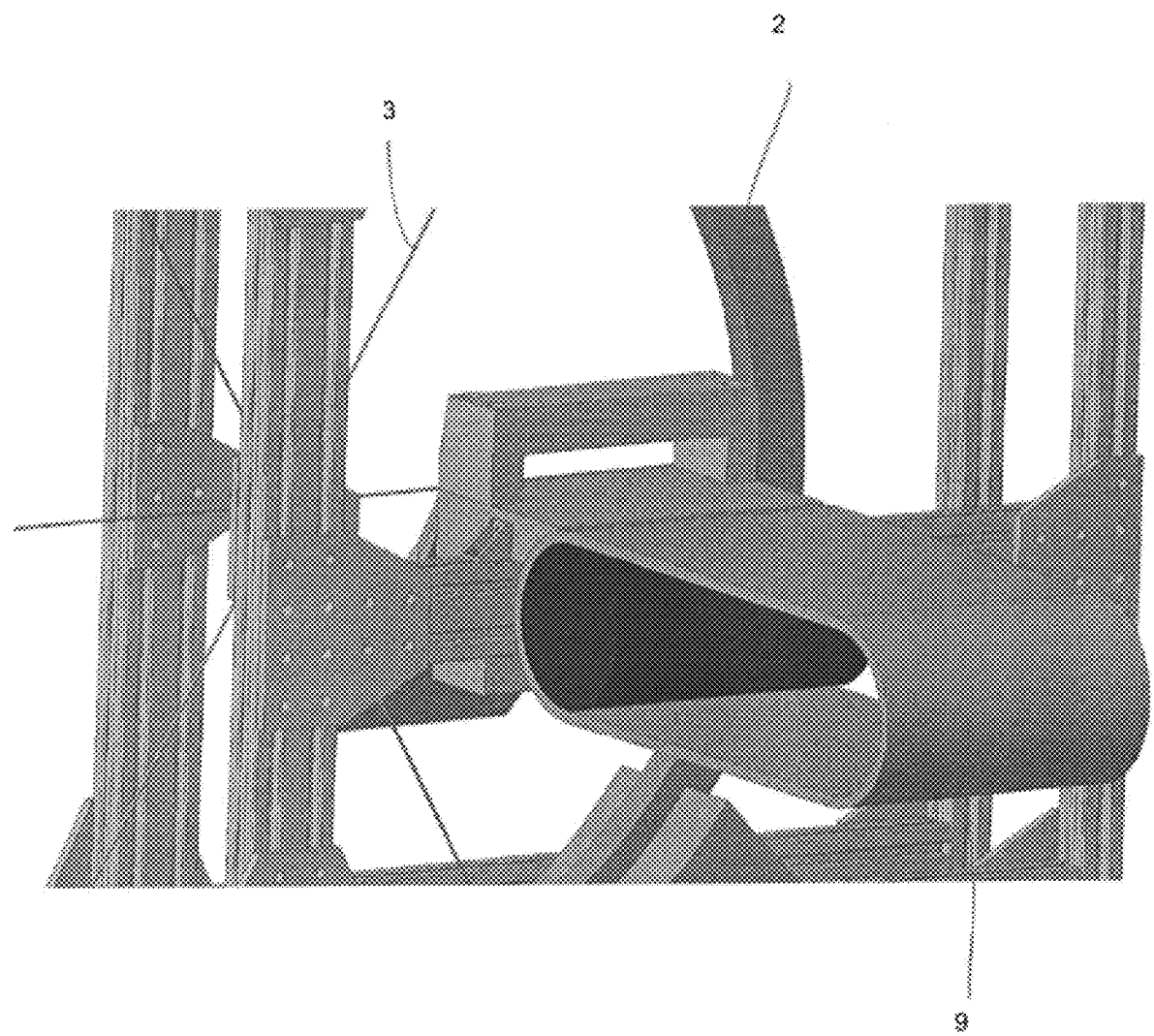
FIG. 8 is a perspective close-up left back view showing the conveyor belt.
Figure 9:
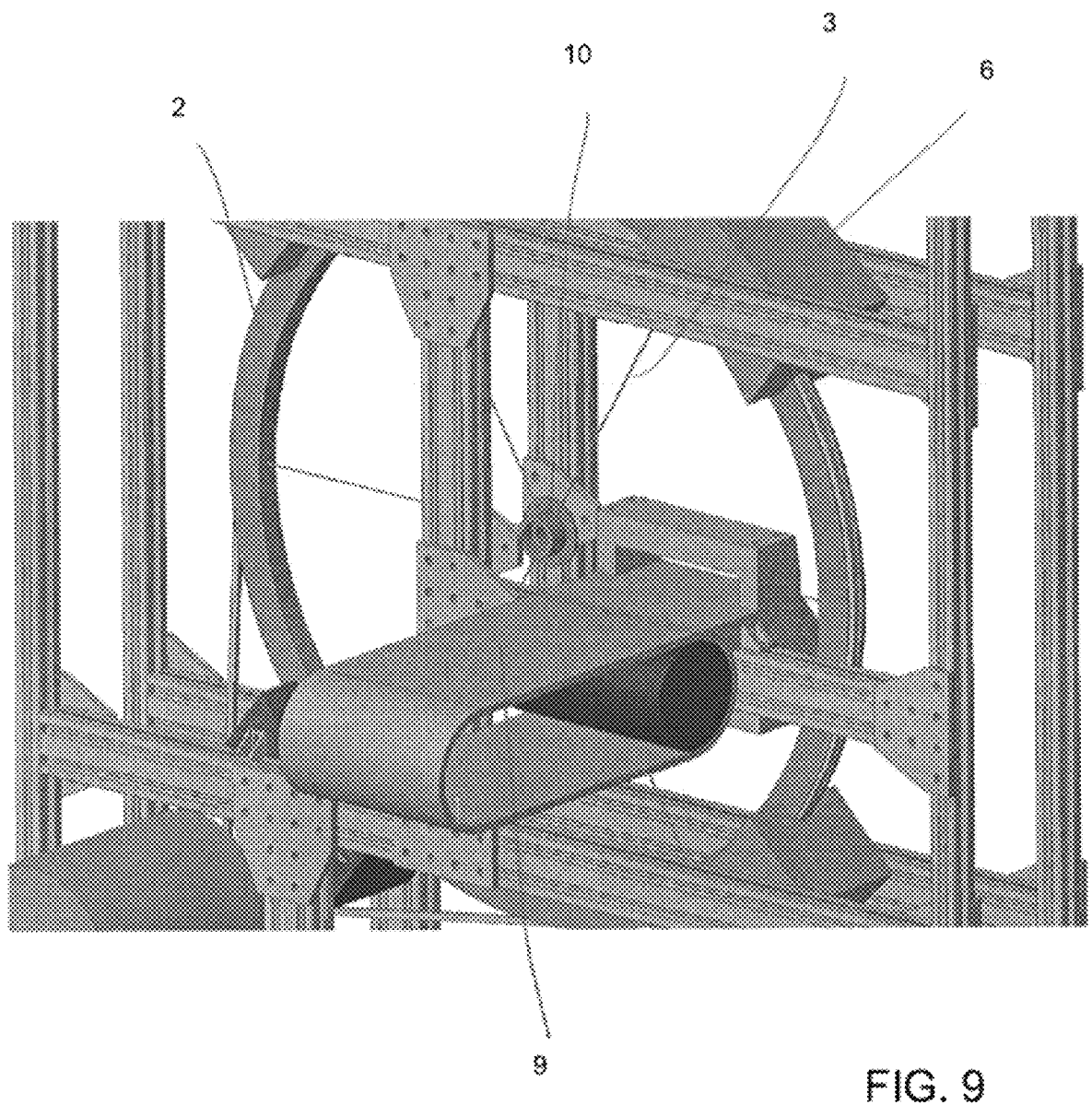
FIG. 9 is a perspective close-up right back view showing the conveyor belt.
Figure 10:
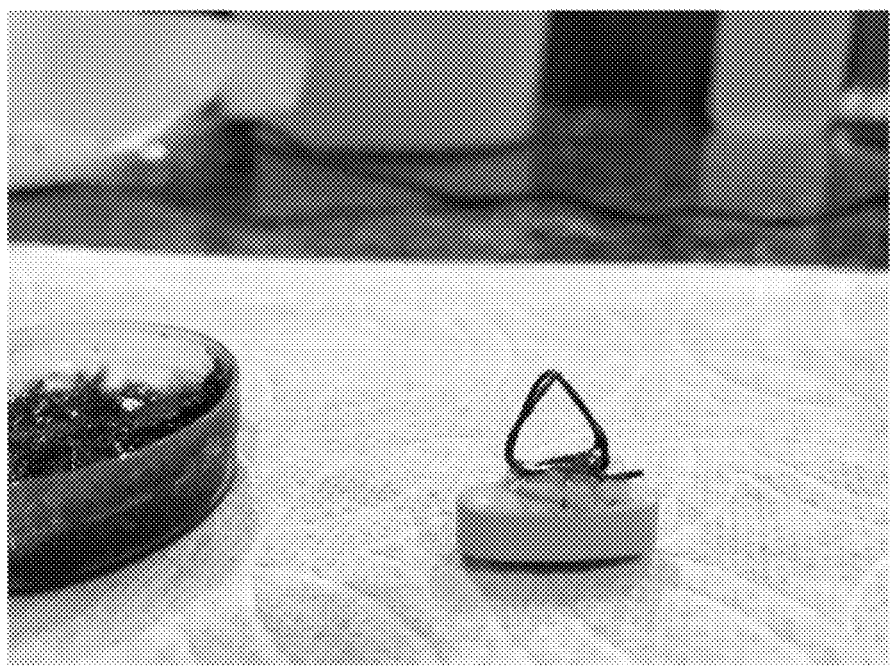
FIG. 10 is a photograph of a scale apparatus for measuring cling of adhesive compositions. A sample of an adhesive portion in a sample cup and an tablet with anchor attachment thereon are shown

Irrespective of the size and shape of the animal treat, the adhesive portion is at least partially exposed through an opening in the outer portion to allow for insertion of the medicament. The opening in the outer portion is sized and configured to allow a human to push an oral medication into the adhesive portion of the treat, for example, by using a finger. For instance, when the animal treat is in the shape of a cylinder, the adhesive portion may be exposed to the surface of the treat composition at one or both ends of the cylinder. Referring to FIGS. 1 and 2, an aspect of an animal treat 100 is shown. The animal treat 100 comprises an adhesive inner portion 110 partially surrounded by an outer portion 120. In FIG. 1 a medication 130 is being inserted into the adhesive 110 through an opening 140 in the outer portion 120.

To prevent adhesion of the inner portions of treats to surfaces and to other treats during storage, the exposed adhesive portion may be partially or entirely covered by a compatible material to reduce surface stickiness, but not seal the exposed section. Alternatively, the exposed adhesive portion can be retracted from an opening in the outer portion to prevent contact of the inner portions to surfaces and other treats during storage.

The adhesive and the outer portions differ in texture, but may also differ in color, taste, nutritional value, and appearance. An adhesive portion may substantially take the shape and completely fill a cavity created within an outer portion. Alternatively, an adhesive portion may partially fill a cavity within an outer portion. For instance, an adhesive portion may fill about 10%, 20%, 30%, 40%, 50%, 60%, 70%, 80%, 90%, or 95% or more of a cavity created within an outer portion. An adhesive portion may conform to the contours of the inner cavity, or may have a shape distinct from the contours of an inner cavity. In one aspect, an adhesive portion conforms to the contours of the inner cavity.

An outer portion can comprise from about 5% to about 95% w/w of the treat. For instance, the outer portion can comprise about 5, 10, 15, 20, 25, 30, 35, 40, 45, 50, 55, 60, 65, 70, 75, 80, 85, 90, or about 95% w/w of the treat. In some aspects, the outer portion comprises from about 40% to about 60% w/w of the treat. Conversely, the adhesive portion can comprise from about 5% to about 95% w/w of the treat. For instance, the adhesive portion can comprise about 5, 10, 15, 20, 25, 30, 35, 40, 45, 50, 55, 60, 65, 70, 75, 80, 85, 90, or about 95% w/w of the treat. In some aspects, the adhesive portion comprises from about 40% to about 60% w/w of the treat.

Palatability of an animal treat may be evaluated using any method of determining the sensory evaluation of a food product. The term "sensory evaluation" may be used to describe a scientific method used to evoke, measure, analyze, and interpret those responses to products as perceived through the senses of sight, smell, touch, taste, and hearing. As will be recognized by individuals skilled in the art, sensory evaluation can include the use a panel of evaluators, wherein test results are recorded based on the responses of the evaluators to the products under test. Statistical analysis may then be employed to generate inferences and insights regarding a product. For a pet food, a panel of evaluators may be pets.

A treat of the present disclosure can be nutritionally complete for a pet. Such nutritional characteristics can be provided by making an animal treat, as a whole, nutritionally complete. For instance, an adhesive portion may provide a protein component of a treat, whereas other nutritional qualities of the treat are provided by the outer portion of the treat. Of course, it will be recognized that some ingredients can perform more than one function. For instance, starch may be used to provide nutritional qualities and also control texture and integrity of a product. Further, sugars may be used as flavoring agents, palatability agents, and as softening agents, and proteins and meats can be used as a palatant, a source of protein, or a flavoring agent.

Dual-textured animal treats maintain textural integrity between the outer portion and the adhesive inner portion. Textural integrity can be maintained for a period ranging from about 1 day to about 4 years or longer. For instance, textural equilibrium can be maintained for about 1, 2, 3, 4, 5, 6, 7, 8, 9, 10, 11, 12, 18, 24, or 36 months or longer. In some aspects, dual-textured treats maintain textural integrity between a rigid outer portion and a semi-solid center portion for about 24 months to about 36 months or longer.

The compositions of the adhesive and outer portions are compatible, or comprise compatible ingredients, such that the textural integrity of the treat can be maintained for extended periods of time. As used herein, the term "compatible," when referring to a composition or ingredient, refers to compositions and ingredients that, when present in one of the portions, is compatible with compositions and ingredients in the other portion such that the textural stability and integrity of the treat is maintained even for extended periods of time. In some aspects, the inner and outer portions of the treat have compatible water activities and starch compositions. While not wishing to be bound by theory, it is believed that compatible water activities and starch compositions of the inner and outer portions maintain the textural stability of the treat to provide an extended shelf life.

As explained above, the water activities of the inner and outer portions can be compatible. This is because significantly different water activities of adjoining compositions of the inner and outer portions cause the moisture in the inner and outer portions to diffuse until equilibrium is reached, thereby altering the texture and functionality of the treat. Conversely, treats comprising compatible water activities of the inner and outer portions extend the textural stability of the animal treat of the present disclosure by preventing diffusion of water between the inner and outer portions.

Quantitatively, water activity ($A_w$) is equal to the vapor pressure of a composition divided by the vapor pressure of pure water under the same conditions. Using this particular definition, pure distilled water has a water activity of exactly one, and the water activity of a food is below one, and is dependent on the degree to which water is bound in a food product. Using this definition, compatible activities of an inner and outer portions refer to water activities of the two portions that vary by than 1, 2, 3, 4, 5, 6, 7, 8, 9, or about 10%.

According to the instant disclosure, when a treat comprises starch, the starch compositions of the inner and outer portions can be compatible. For instance, the inner and outer portions can have similar concentrations of starch, similar compositions of various starches, a similar or identical starch content, and combinations thereof. As explained further below, compatibility of the starch contents of the inner and outer portions can maintain similar retrogradation and moisture management between the two portions.

In some aspects, compatible starch compositions of the inner and outer portions comprise a high content of amylopectin or a high ratio of amylopectin to amylose. Amylose has a high tendency to retrograde, while amylopectin has a low tendency to retrograde. Retrogradation of starch leads to physical shrinking of the starch mass. If a starch contracts, the integrity of the treat can be compromised. For example, a starch content of the outer portion having a high amylose content can contract, squeeze, and expose the adhesive portion, causing the treats to stick together. A starch high in amylopectin can be a starch from rice, waxy rice, corn, waxy maize, waxy potato, potato, tapioca or combinations thereof for viscoelastic texture. A high ratio of amylopectin to amylose in the starch composition can range from about 60% amylopectin:40% amylose, to about 99% amylopectin: 1% amylose.

B. Outer Portion of an Animal Treat Composition.

The outer portion of an animal treat comprises a non-sticky semi-rigid texture to the animal treat. A semi-rigid texture of an outer component may be any soft or chewy, but rigid, non-sticky texture that may appeal to a pet, and that can facilitate handling of the treat by a user when inserting a medication. For instance, a semi-rigid outer portion may be sufficiently rigid to provide a soft or firm texture, or a chewy texture. In some aspects, a rigid outer portion has a treat-like texture. In other aspects, the semi-rigid texture can be sufficiently rigid to break when flexed.

In some aspects, the outer portion is soft to firm in texture. A soft outer portion may be ductile such that an animal's teeth can penetrate into the outer portion without readily crumbling, breaking, or tearing, and may require multiple chews or compressions to break down. A firm texture of the outer portion may be stiff and break or crack upon an animal's teeth penetrating into the outer portion as the treat is consumed. The particular characteristics of the chew can be controlled such that the ductility characteristics can vary based on the desired finished characteristics. As a result of the wide variations in chewing aggressiveness between different animals and breeds of animals, it is desired to have a range of ductile characteristics. It is also desired for the animal treats to be such that ductile characteristics can be changed to provide for various chew durations by a typical animal. Thus, the animal treat can be constructed such that it has a greater or shorter longevity dependent upon the desired final product.

Thickness of an outer portion can and will vary depending on the desired strength and durability, texture, shape, and method of manufacture of an outer portion. For instance, thickness of an outer layer may be about 0.1 to about 10 mm thick or from about 1 to about 4 mm. In one aspect, the thickness ranges from about 2.5 to about 3.5 mm.

In some aspects, an outer portion of an animal treat has a water content of less than about 50%, a water content ranging from about 1% to about 45%, or a water content of less than about 25%.

In some aspects, an outer portion of an animal treat can have an $A_w$ of less than about 0.9. For instance, the outer portion of the animal treat of the present disclosure can have an $A_w$ of about 0.10, 0.20, 0.30, 0.40, 0.50, 0.60, 0.70, 0.80, or about 0.90. In some aspects the outer portion of the animal treat has an $A_w$ ranging from about 0.40 to about 0.90 or from about 0.50 to about 0.70. In one aspect, the $A_w$ of the outer portion ranges from about 0.40 to about 0.85. In another aspect, the $A_w$ of the outer portion is less than 0.8, or ranges from about 0.70 to about 0.80. As explained above, a water activity of the outer portion is compatible with the water activity of the adhesive portion. Compatible water activities are water activities that are substantially analogous. For instance, the water activity of the adhesive portion can vary by no more than 1, 2, 3, 4, 5, 6, 7, 8, 9, or about 10% from the water activity of the outer portion.

The outer portion of the animal treat is typically formulated with one or more edible textural agents, one or more sugars, one or more flavoring agents, one or more edible acidulants, preservatives, and may include a gelling agent, salt, an emulsifier or surfactant, a colorant, and an antioxidant.

An edible textural agent is an important ingredient making up the outer portion of the animal treat. The edible textural agent is generally a dry ingredient that, when mixed with wet ingredients, acts as a binder or thickener for the wet and dry ingredients. In some aspects, the edible textural ingredient is a flour or starch. Any flour suitable for use in animal nutrition is generally acceptable within the outer portion of the animal treat provided the flour has a high amylopectin content, and provided the starch is compatible with a starch content of the inner portion. The flour may be processed or unprocessed and in some cases is pre-gelatinized. Similarly, any starch, including potato and corn starches, may be used as a textural agent alone or in combination with a flour. The edible textural agent is present in the outer portion of the animal treat in an amount compatible with an amount of starch found in the inner portion. For instance, the outer portion comprises an amount of starch ranging from about 10% w/w to about 90% w/w of the outer portion of the animal treat composition, or from about 20% w/w to about 50% w/w of the outer portion of the animal treat composition.

One or more edible acidulants can be included in the animal treat to improve the flavor and adjust pH to optimum levels for mold inhibitor functionality. The acidulant can be an edible organic acid, an edible inorganic acid, an edible acid salt, or combinations thereof. Examples of edible organic acids that can be used are citric acid, acetic acid, tartaric acid, lactic acid, malic acid, succinic acid, adipic acid, fumaric acid, propionic acid, and sorbic acid. Examples of edible inorganic acids that can be used are phosphoric acid, hydrochloric acid, and sulfuric acid. Examples of edible inorganic salts are monobasic sodium phosphate, monocalcium phosphate, aluminum sulfate, aluminum calcium sulfate, and aluminum sodium sulfate. In some aspects, the present invention includes acetic acid, acidified calcium sulfate, or lactic acid in an amount equal to or less than about 1.5% of the outer portion of the animal treat. Alternative aspects may contain different acidulants depending on the desired tartness of the animal treat composition.

Salt may also be present in the animal treat composition as a flavor enhancer in an amount equal to or less than about 1% w/w of the outer portion of the animal treat. Other ingredients may be added that can enhance the palatability, nutritional quality, and appearance of the treat. For instance Flax Seed Meal may be added as a nutritive enhancement for its Omega Fatty Acids and functional fiber.

A gelling agent can be used to increase the rigidity and tensile strength, and modify texture the of the outer portion of the animal treat composition and to help ensure that the outer portion maintains its shape from production of the animal treat to its consumption by the animal. Gelling agents include both natural and synthetic gelling agents such as gelatin, acacia, alginic acid, bentonite, carbomers, carboxymethyl cellulose, ethylcellulose, hydroxyethyl cellulose, hydroxypropyl cellulose, magnesium aluminum silicate, methylcellulose, poloxamers, polyvinyl alcohol, sodium alginate, tragacanth, and xanthan gum. The gelling agent may be present in the outer portion in an amount ranging from about 0.2% w/w to about 5% w/w of the outer portion of the animal treat composition and may vary depending on the type of gelling agent. When gelatin is used, it is typically used in an amount ranging from about 0.1% to about 10% w/w to the outer portion, preferably from about 1% to about 3% w/w to the outer portion.

The flavor of the outer portion of the animal treat composition may also be enhanced by the use of one or more palatability enhancers. Palatability enhancers are formulation ingredients designed to improve the sensory experience for the animal by providing the formulation with an improved smell, taste, texture, or visual appearance. Palatability enhancers are typically proprietary mixtures of ingredients sold by, for example, ABF International® or Kemin®

Industries. The amount of palatability enhancer used in the outer portion of the animal treat is typically less than 5% w/w, or more preferably less than 3% w/w. In a preferred aspect, the palatability enhancer is AFB Optimizor™, sold by ABF International, St. Charles, MO.

An animal protein: fresh, frozen, processed or stabilized animal meat may provide an appealing flavor and palatability to the animal treat in addition to certain nutritive benefits. Animal protein can be used to give the outer portion of the animal treat a flavor that is palatable to the target animal. Alternatively, an animal-derived meal or dried meat can be used. Suitable animal-derived meals include poultry meal, bone meal, fish meal, fish processing by-products, meat meal, meat and bone meal, poultry by-product meal, feather meal, and combinations thereof. The processed or stabilized animal meat or meal may be present in the outer portion of the animal treat in an amount ranging from about 1% to about 20% of the outer portion, preferably from about 1.5% to about 15% of the outer portion. In one preferred aspect, flavor is provided to the outer portion of the animal treat by incorporation of about 5% poultry meal and about 6% w/w stabilized chicken meat. In some aspects, the meaty flavor of the processed or stabilized animal meat or meal is enhanced by a smoke flavoring ingredient, which is incorporated into the outer portion in an amount equal to or less than about 1% w/w. Charsol® C-10, sold by Aceto Corporation, can be a smoke flavoring ingredient. It will be recognized that proteins and meats can be used as a palatant, a source of protein, or a flavoring agent, etc.

The outer portion of the animal treat is also typically formulated with an edible emulsifier or surfactant such as a lecithin, a mono- or di-glyceride or an ester thereof, a sucrose ester, a sorbitan ester, or any other edible emulsifier commonly used in food or animal treats. In one aspect, a dried yolk is used. When the edible emulsifier is a mono- or di-glyceride, it may be natural or synthetic. Naturally derived mono- and di-glycerides may be obtained from a variety of sources such as sunflower, rapeseed, palm, or soya bean oil. The emulsifier or surfactant is present in the outer portion formulation in an amount ranging from about 0.5% to about 5% w/w to the outer portion. In one aspect, lecithin is used in combination with a small amount of Dimodan® emulsifier, obtained from Danisco, Madison, WI.

One or more sugars may be used in the outer portion of the animal treat to give the animal treat a desired sweetness and texture. As explained above, sugars may be used as flavoring agents, palatability agents, and as softening agents. The sugar can be any type of starch hydrolysate such as corn syrup, rice syrup, tapioca syrup, or derivatives such as high fructose corn syrup, high maltose corn syrup, glycerin or an acid-enzyme corn syrup. Other useful sugars are dextrose, glycerin, propylene glycol, maple sugar, maltose, sucrose, lactose, xylotol, glucose, and fructose. Granulated white and brown sugar as well as maltodextrin or dried corn syrup can be used. In addition, a combination of sugars can be used. The sugar may be present in the outer portion of the animal treat in an amount ranging from about 1% to about 25% w/w to the outer portion, from about 15% to about 30% w/w, or about 10% to about 20% w/w of the outer portion. In one aspect, the outer portion comprises from about 10% w/w to about 20% w/w glycerin, and from about 2.5% w/w to about 7% w/w rice syrup of the outer portion.

The outer portion of the animal treat may further include colorants such as caramel color, iron oxide, titanium dioxide, FD&C dyes, aluminum lake colors, natural pigments, or combinations thereof. The colorant is added to the outer portion of the animal treat in an amount ranging from about 0.5% to about 1.5% w/w to the outer portion. The amount depends on the colorant used and the color desired. In one aspect, the colorant is Caramel Color P330. In another aspect Black Malted Barley from Briess Malt & Ingredients is used to add to the color of the outer portion.

The outer portion may additionally contain one or more preservatives. A preservative inhibits microbial growth and/or preserves freshness by preventing degradation of the animal treat ingredients. Preservatives include benzoic acid, sorbic acid, propionic acid, diethyl pyrocarbonate, sorbate salts, and menadione, including the salts and esters thereof, or cultured products and cultured by-products that deliver mold inhibiting properties. The preservative is typically present in the outer portion of the animal treat in an amount less than about 1% w/w of the outer portion. The outer portion of the animal treat can contain cultured skim milk as a preservative.

Typically in addition to a preservative, the outer portion of the animal treat will contain an antioxidant. Antioxidants also preserve the freshness of certain ingredients, especially those prone to oxidative degradation. Suitable antioxidants include, but are not limited to, ascorbyl palmitate, ascorbic acid, butylated hydroxyanisole (BHA), butylated hydroxytoluene (BHT), cetyl gallate, chlorogenic acid, 6-ethoxy-1, 2-dihydro-2,2,4-trimethylquinoline (ethoxyquin), ethyl gallate, propyl gallate, tocopherols (i.e., alpha-, beta-, gamma- and delta-tocopherol), tocotrienols (i.e., alpha-, beta-, gamma- and delta-tocotrienols), tertiary butyl hydroquinone (TBHQ), thiodipropionic acid, trihydroxy, vitamin E, vitamin K, and combinations thereof. The antioxidant is present in an amount sufficient to stabilize the treat composition for the pre-dated shelf life. Typically, the antioxidant makes up less than 0.5% w/w of the outer portion of the animal treat. The antioxidant can be a tocopherol. In another aspect, the antioxidant is supplied to the outer portion of the animal treat composition by Nature Ox™, sold by Kemin Industries, Des Moines, IA, which is a mixture including tocopherol.

C. Adhesive Inner Portion.

The adhesive portion of the dual-textured animal treat composition is a sticky semi-solid mass characterized by a sufficient viscosity that is solid but malleable with minimal pressure. For instance, the adhesive portion can have the texture of a firm gel, a paste, or have an elastic texture. The adhesive portion is designed to receive an oral medication. The oral medication is inserted into the semi-solid mass with minimal force. The composition's adhesive portion is also characterized by adhesiveness that allows the adhesive portion to adhere to the oral medication and to prevent the animal from separating the oral medication from the animal treat composition.

The inner portion has an adhesive strength capable of retaining a medication when administered to an animal and prevent the animal from expelling the medication. The adhesive strength can be measured by, e.g., attaching a medication to a composition of an inner portion, and determining the amount of the composition adhered to the medication when the medication is removed from the inner portion. The adhesive strength of the inner portion can and will differ depending on the composition of the inner portion and the medication, among other variables.

The adhesive portion of the animal treat can be formulated with one or more sugars, a viscosity enhancing agent, a gelling agent, a flavoring agent, an edible emulsifier or surfactant, an edible acidulant, a preservative, a salt, water, an antioxidant and combinations thereof. Sugars, viscosity enhancing agents, gelling agents, flavoring agents, edible emulsifiers or surfactants, edible acidulants, preservatives, and antioxidants can be as described above.

The adhesive portion comprises a fat content of about 5% w/w or lower, 3% w/w or lower, 2% w/w or lower, 1% w/w or lower, or about 0.5% w/w or lower of the adhesive portion. While not wishing to be bound by theory, a low fat content of the adhesive portion as described herein contributes to the stickiness of the adhesive portion and the adhesive nature that the treat is capable of achieving. Further, a low fat content reduces the need for an emulsifier in the adhesive portion.

In contrast to the outer portion, the adhesive portion of the animal treat composition comprises a significantly higher amount of water and sugar. This higher amount of sugar and water significantly contributes to the balance of properties exhibited by the treat to provide the improved characteristics of the treat.

As noted previously, the adhesive portion of the animal treat is formulated with one or more sugars. The sugar provides sweetness to the adhesive portion of the animal treat, provides water binding and texture softening, and also adds to the stickiness of the adhesive portion, which is important for holding the oral medication to the adhesive portion of the treat. Sugars suitable for the adhesive portion of the animal treat composition can be dried or liquid starch hydrolysates such as: corn syrup, rice syrup, tapioca syrup, or molasses, honey, dextrose, glycerin, propylene glycol, maple sugar, maltose, sucrose, lactose, xylitol, glucose, or fructose used individually or in combination. Granulated white or brown sugar may also be used. The adhesive portion can comprise from about 5% w/w to about 50% w/w, or about 25% w/w to about 50% w/w of one or more sugars. The sugars can be chosen from glycerin, liquid or dried starch hydrolysates such as corn syrup, rice syrup, tapioca syrup, or other sugars such as molasses, honey, sugar, dextrose, propylene glycol, and combinations thereof w/w to the adhesive portion. The adhesive portion of the animal treat can contain from about 5% w/w to about 50% w/w or from about 20% w/w to about 50% w/w of the sugar w/w of the adhesive portion. The adhesive portion of the animal treat can also contain from about 25% w/w to about 45% w/w of the sugar. In one aspect, the adhesive portion of the animal treat contains from about 10% w/w to about 20% w/w dried corn syrup, from about 10% w/w to about 20% w/w granulated sugar, and from about 5% w/w to about 10% w/w maltodextrin of the adhesive portion. In another aspect, the adhesive portion of the animal treat composition contains about 30% w/w of a sugar that is a mixture of granulated sugar and dry corn syrup. And still in another aspect, the adhesive portion of the animal treat contains 10% w/w dried molasses, 4% w/w dried rice syrup, 16% w/w glycerin, and 14% w/w liquid rice syrup. In one aspect, the adhesive portion contains from about 10% to about 20% w/w glycerin of the adhesive portion, from about 10% w/w to about 20% w/w corn syrup of the adhesive portion, and from about 1% w/w to about 5% w/w propylene glycol of the adhesive portion. In another aspect, the adhesive portion contains from about 5% w/w to about 25% w/w, about 10% w/w to about 20% w/w or about 12% w/w to about 18% w/w glycerin of the adhesive portion, from about 12% w/w to about 18% w/w corn syrup of the adhesive portion, and from about 1% w/w to about 3% w/w propylene glycol of the adhesive portion. In another aspect, the adhesive portion contains about 16% w/w of corn syrup, about 2.5% w/w propylene glycol, and about 13% w/w of glycerin.

The adhesive portion can comprise 15% w/w or more water, 20% w/w or more water, 35% w/w or more water, 40% w/w or more water, 34% w/w or more water to the adhesive portion. In some aspects, the adhesive portion comprises from about 30% w/w to about 40% w/w water. In other aspects, the adhesive portion comprises from about 32% w/w to about 37% water w/w. In yet other aspects, the adhesive portion comprises 15% w/w or more water.

The adhesive portion of the animal treat may also contain a viscosity enhancing agent. A viscosity enhancing agent, in the context of the invention, increases the viscosity of the adhesive portion of the animal treat so that the adhesive portion is semi-solid, but malleable when pressure is applied. The adhesive portion is a semi-solid mass. In the absence of pressure, the adhesive portion maintains the shape that it is extruded or molded into; when pressure is applied, the adhesive portion is malleable such that an oral medication can be pushed into the adhesive portion. The viscosity enhancing agent may be chosen from a variety of viscosity enhancing agents such as garbanzo bean flour, arrowroot flour, corn flour, corn starch, wheat flour, rice flour, katakuri starch, potato starch, sago, and tapioca flour. For the purpose of this technology the viscosity enhancing agents include all forms of the sources; whole or partial and all species of the source. The viscosity enhancing agent is present in the adhesive portion of the animal treat in an amount ranging from about 10% w/w to about 23% w/w to the adhesive portion of the animal treat. In one aspect, the viscosity enhancing agent is a corn starch sold under the trade name Ultra-sperse® A. In another aspect a combination of Ultra-sperse® A and rice flour is used. Further, in another aspect, a corn starch is used sold under the trade name Mira-Thik® 603.

The adhesive portion may also contain a gelling agent which adds to the viscous properties of the adhesive portion. The gelling agents of the adhesive portion may be the same as the gelling agents described in Section I(B). In one aspect, gelatin is the gelling agent and it is included in the adhesive portion of the animal treat in about 1% w/w to the adhesive portion of the animal treat.

The adhesive portion of the animal treat composition also may contain one or more flavoring agents, to make the treats more appealing. Flavoring agents include but are not limited to animal proteins, animal digests, meat meals, animal by-products, flavorings, compounded flavors, extractives, flavor enhancers, vegetables, fish proteins, fish by-products, crustation proteins, crustation by-products, and any additive that delivers flavor or palatability enhancement. In one aspect, the flavoring agent is added to the adhesive portion of the animal treat in an amount ranging from about 2% w/w to about 10% w/w.

The adhesive portion of the animal treat can also be formulated to include an edible emulsifier or surfactant such as egg yolk, a lecithin, a mono- or di-glyceride or an ester thereof, a sucrose ester, a sorbitan ester, or any other edible emulsifier commonly used in food or animal treats. The emulsifier or surfactant may be as described in Section I(B). When used in the adhesive portion of the animal treat composition, it is formulated in an amount less than about 1% w/w. In some aspects, the emulsifier is Dimodan® brand emulsifier, obtained from Danisco, Madison, WI.

The adhesive portion of the animal treat may also contain a palatability enhancer, an edible acidulant, a preservative, a salt, and an antioxidant as described in Section I(B). As explained above, the adhesive portion contains compatible starch composition and water activities as compared with the outer portion of the treat. The compatibilities contribute to maintaining similar retrogradation and moisture management between the two portions. If compatibility does not exist, the outer portion can retrograde more than the adhesive portion causing the adhesive portion to be squeezed out the ends of the treat. Similarly, if water activities are not similar, the moisture will equilibrate and move from one portion to the other portion, causing physical changes and potential swelling or shrinking causing distortions, cracking of the outer portion, or squeezing of the adhesive portion out the ends of the outer portion.

The inner portion can be acidified to improve elasticity of the adhesive portion. Acidulants suitable for use to acidify the inner portion can be as described above in Section I(B) above. Any concentration of acidulant can be included in the animal treat, provided the pH of the inner portion is acidified to a desired pH. In some aspects, the inner portion of the treat is acidified. For instance, the inner portion can be acidified to a pH ranging from about 4.5 to about 5.5, a pH of 5.3 or less, a pH of 5 or less, a pH of 3 or less, or a pH ranging from about 2 to about 3. In other aspects, the inner portion can further comprise enzymes that can improve elasticity of the adhesive portion. Non-limiting examples of enzymes include amylases, isoamylases, proteases, and combinations thereof. In some aspects, the inner portion comprises monoglycerides to improve elasticity of the adhesive portion. The concentration of monoglycerides can and will vary depending on the composition of the treat, the desired elasticity of the treat, the animal for which the treat is intended, and the medication to be administered, among other variables. Any concentration of monoglycerides can be used to improve elasticity provided the inner portion maintains the desired adhesive properties.

II. Method of Providing an Oral Medication to an Animal

In another aspect, the present disclosure encompasses a method for administering an oral medication to an animal using the animal treat described in Section I above. The method comprises inserting an oral medication into the adhesive portion of the animal treat and administering the medicated treat to the animal to the animal. The animal can be a companion animal such as a dog or a cat. The oral medication can be any form of oral medication such as a tablet, capsule, soft gel, or pill.

The method of providing the oral medication to an animal is beneficial because the animal treat composition adheres tightly to the oral medication such that once inserted into the adhesive portion, the adhesive portion adheres to the oral medication, and an animal cannot remove the oral medication from the animal treat composition.

III. Method for Preparing an Animal Treat Composition

In yet another aspect, the present disclosure encompasses a method for preparing the animal treat composition described herein. A method may comprise injection molding, extrusion, co-extrusion, rotary molding, compression molding, sheeting, and sheet casting.

In one aspect, a method comprises obtaining or having obtained an adhesive portion and an outer portion, and using the outer portion to partially or fully cover the adhesive portion, thereby forming the dual-textured animal treat. The inner and outer portions can be formed using any method known in the art for forming and shaping a food or feed composition.

In another aspect, a method comprises extruding a first food material and a second food material. The first food material can be co-extruded at the same time with a second food material.

In one aspect, a method of forming an animal treat comprises co-extruding the inner and outer portions to form a co-extruded treat. The method can comprise providing a first food material for forming a semi-solid adhesive portion; providing a second food material for forming a semi-rigid outer portion; providing a co-extrusion device; co-extruding the first and second food materials to form a co-extruded stream such that an outer rigid component is at least partially surrounding an inner semi-solid component; and dividing or cutting the extrudate into portions to form the dual-textured treat.

Co-extrusion devices capable of co-extruding a dual-textured food product comprising a soft adhesive portion and a semi-rigid outer portion are known in the art. A co-extrusion device suitable for producing a treat of the present disclosure is capable of extruding ingredients of an adhesive portion and extruding ingredients of an outer portion around and at least partially surrounding the adhesive portion to form food products such that an outer rigid portion is distributed about an inner semi-solid portion. Such a device generally comprises: a first extruder for extruding an adhesive portion; a second extruder for extruding an outer portion; a manifold for combining the product of the first and second extruders and a die assembly for forming a co-extruded stream such that an outer semi-rigid component at least partially surrounds an inner semi-solid component.

Generally speaking, extruders are devices which include an elongated, tubular barrel, a material inlet at one end of the barrel, and a restricted orifice adjacent the remaining end thereof. One or more elongated, axially rotatable, flighted extrusion screws are situated within the barrel and serve to transport material along the length of the barrel. One class of extruders is single screw extruders, which include a single, elongated extruder screw within a substantially circular barrel. Another general class of extruders is the so-called twin screw extruders, which have a pair of juxtaposed elongated, flighted screws within a complemental barrel having a pair of side-by-side, frustocylindrical sections. The screws in such a twin screw device may be counter-rotating (i.e., the screws rotate in an opposite direction relative to each other), or co-rotating (i.e., both screws rotate either clockwise or counterclockwise). A twin screw extruder is capable of extruding a moistened food mixture under pressure, self-generated heat and added heat sufficient to cook a food mixture, or under both pressure and heat. Co-extrusion devices which may be used to co-extrude center-filled foods are known in the art and may be as disclosed in, for instance, U.S. Pat. Nos. 3,241,503; 3,480,445; 3,499,766; and 4,275,647, the disclosures of all of which are incorporated herein in their entirety by reference.

When a process comprises using a co-extrusion device, the device comprises a first extruder for extruding a semi-solid inner component, and a second extruder for extruding an outer component. The second extruder can be capable of extruding a moistened food mixture under heat sufficient to cook the food mixture, and to be extruded in a semi-rigid ready-to-eat semi-moist form. In some aspects, both extruders are twin-screw extruders. A co-extrusion device used in a process for preparing the animal treat composition of the present disclosure can also comprise a means for temperature increase in addition to the viscous dissipation of mechanical energy and thermal transfer from the walls of a twin-screw extruder. Additional means for temperature increase are well known in the art, and may include the introduction of steam either into a pre-conditioner or directly into the barrel of an extruder.

The inner and/or outer components can be cooked during extrusion, for example, by subjecting the mixtures to elevated temperatures. In some aspects, a starch is unmodified, and is cooked during the extrusion process. In some aspects, the components may be subjected to a temperature of more than 100° C. in the extrusion process. In one aspect, the components are subjected to a temperature of about 100° F. to about 300° F. or about 155° F. to about 210° F.

A device of the present invention can further comprise a means for cutting a co-extruded animal treat which cuts co-extruded streams into individual discreet product pieces, a means for cooling a co-extruded animal treat, and a means for coating sticky portions of the treat exposed during cutting with material to cover the sticky surface, and keep co-extruded and cut animal treat pieces from sticking to one another. A device can be as described in Section IV below.

In some aspects, a means for coating sticky portions of the treat are particulate material, such as flavor beads. In some aspects, the flavor beads have a size ranging from about 0.1 mm to about 5 mm, can be 1, 2, 3, 4, 5 mm in size or less, or have a size ranging from about 0.1 mm to about 1 mm. A composition of the particulate material can be as described in Example 5.

As described in Section I(A) above, an adhesive portion can completely fill a cavity created within an outer portion, or an adhesive portion may partially fill a cavity created within an outer portion. Additionally, in another element of this technology, the outer portion can only partially cover the adhesive portion, allowing the adhesive portion to be exposed on one, two, or three sides of an animal treat. When an adhesive portion completely fills a cavity created within an outer portion, it is believed that a certain pressure on the flow of core material in the radial direction is necessary to completely and tightly fill the void center volume of an extruded outer portion. As such, material of an adhesive portion can be injected into an outer portion during co-extrusion at a volumetric flow rate slightly greater than needed to fill the void center volume of the shell. Alternatively, material of an adhesive portion is injected into an outer portion during co-extrusion at a volumetric flow rate slightly less than needed to fill the void center volume of the shell to partially fill a cavity within an outer portion.

IV. Treat Cutting Device

In yet another aspect, the disclosure provides a device for cutting the product. In some aspects, the product is an extruded product. In some aspects, the product is a food product. In other aspects, the product is a co-extruded product. In another aspect, the product is a co-extruded food product. In one aspect, the product is a dual-textured treat for administering a medication to an animal described in Section I above. In some aspects, the inner portion of the dual-textured food product is adhesive, and the adhesive inner portion of the cut piece is exposed.

The device is especially useful for cutting a sticky extruded product without the product sticking to the device, even if the product is warm. Existing cutting systems used in the extrusion industry utilize either hard, fixed wedge blades, spring plate blades, or knife blades fixed to spinning fly knives. Using these cutting systems, an adhesive product sticks readily to any surface it contacts (especially when hot) and as a result, all knives used to attempt to cut theses pilling treats immediately build up with the adhesive product and quickly eliminate any ability to cut successfully. Even when a lubricating liquid or anti-sticking spray is applied to the knife blades, the adhesive product quickly builds up on the blades and the system fails to cut the product. A special cutting system is needed to successfully cut a sticky product such as the pilling treat having a sticky center as disclosed herein.

Referring to the drawings in FIGS. 3-9, the cutting device 1 comprises a cutting wheel 11 comprising cutting wires 3 strung between an axle 10 and an outer rim 2. In some aspects, the cutting wires 3 are spaced evenly at the outer rim 2. The cutting wheel 11 is rotatably attached to a frame 5 at the axle 10 such that the cutting wheel 11 is capable of rotating about the axle 10. The cutting wheel 11 can comprise 1, 2, 3, 4, 5, 6, 7, 8, 9, 10 or more cutting wires 3. In some aspects, the cutting wheel 11 comprises 6 cutting wires. The diameter of the cutting wires 3 can range from about 0.1 to about 10 mm in diameter. A smaller surface area of a wire provides a cleaner cut. In some aspects, the cutting wires 3 have a diameter of about 3 mm or less. In some aspects, the cutting wires 3 have a diameter of about 2 mm or less. The cutting device 1 can further comprise tensioners (not shown) for tensioning the wires 3 for continued efficient cutting of the food material. For instance, the tensioner can be similar to a guitar tensioner.

The device 1 further comprises a means for rotating the cutting wheel 12 about the axle 10. The means can be a belt 8 movably engaging the cutting wheel 11, and movably engaging a means of moving the belt 8, such as a motor 7. The belt 8 can engage the cutting wheel 11 at the outer rim 2 of the cutting wheel 11. The motor 7 can be attached to the frame 5.

The cutting device 1 can further comprise a means for carrying the extruded product (not shown) and positioning the product for cutting by the cutting wires 3. The means can be a conveyor belt 9, such that the conveyor belt 9 conveys the extruded product perpendicularly to the cutting wheel 11 and positions the extruded product to pass through the cutting wheel 11, thereby disposing the product for cutting by the cutting wires 3. Each cutting wire 3 cuts the extruded product conveyed by the conveyer belt 9 into a cut piece (not shown) of the extruded product when the cutting wheel 11 rotates about the axel 10.

The cutting device 1 can further comprise a means for delivering the cut pieces of product. The means can be a chute 4 attached to the frame 5, and disposed in a manner to catch the cut pieces of the extruded product after the product is cut.

In some aspects, the device 1 further comprises means of delivering a particulate material (not shown) to the product at the cutting wire 3, during cutting of the product. In some aspects, the means of delivering a particulate material is one or more container 6 attached to the outer rim 2 of the cutting wheel. The particulate material can be flavor bits as described above, or can be a compatible powder like magnesium stearate to coat the exposed adhesive portion and prevent adhesion of the inner portions of treats to surfaces and to other treats during storage. In some aspects, the device 1 comprises one or more container 6 attached to the outer rim 2 of the cutting wheel 11, wherein each container 6 is operable to deliver the particulate material to the extruded product at the cutting wire 3 when the cutting wheel 11 rotates about the axel 10. In some aspects, the inner portion of the dual-textured food product is adhesive, and the adhesive inner portion of the cut piece is exposed. In some aspects, the inner portion of the dual-textured food product is adhesive, the adhesive inner portion of the cut piece is exposed, the particulate material is magnesium stearate powder, and delivering the magnesium stearate to the to the extruded product at the cutting wire 3 coats the exposed adhesive portion of the cut piece. In other aspects, the inner portion of the dual-textured food product is adhesive, the adhesive inner portion of the cut piece is exposed, the particulate material is flavor bits, and delivering the magnesium stearate to the to the extruded product at the cutting wire 3 coats the exposed adhesive portion of the cut piece.

The number of cutting wires 3, the speed of introducing the product to the device 1, as well as the speed of rotation of the cutting wheel 11 can be optimized to cut the product to a desired length. Further, the timing of movement of the cutting wheel 11 can be synchronized with the extrusion rate of a product to provide individual co-extruded products having an approximately predetermined size and weight.

Definitions

Unless otherwise defined, all technical and scientific terms used herein have the same meaning as is commonly understood by one of skill in the art to which this invention belongs at the time of filing. If specifically defined, then the definition provided herein takes precedent over any dictionary or extrinsic definition. Further, unless otherwise required by context, singular terms shall include pluralities, and plural terms shall include the singular. Herein, the use of "or" means "and/or" unless stated otherwise. All patents and publications referred to herein are incorporated by reference.

As used herein, the terms "about" and "approximately" designate that a value is within a statistically meaningful range. Such a range can be typically within 20%, more typically still within 25%, and even more typically within 50% of a given value or range. The allowable variation encompassed by the terms "about" and "approximately" depends on the particular system under study and can be readily appreciated by one of ordinary skill in the art.

As used herein, "a" and "an" mean one or more, unless otherwise indicated.

As used herein, "animals" refers to non-human vertebrates. Especially contemplated are companion animals. Examples of companion animals include, but are not limited to, cats, dogs, rabbits, ferrets, gerbils, hamsters, chinchillas, guinea pigs, and domesticated rats.

As used herein, the term "ductility" is defined as a cohesive material whose shape can be modified under force or after being stretched, and may have a propensity to return to its original shape.

Although the invention described herein is susceptible to various modifications and alternative iterations, specific aspects thereof have been described in greater detail above. It should be understood, however, that the detailed description is not intended to limit the invention to the specific aspects disclosed. Rather, it should be understood that the invention is intended to cover all modifications, equivalents, and alternatives falling within the spirit and scope of the invention as defined by the claim language.

EXAMPLES

All patents and publications mentioned in the specification are indicative of the levels of those skilled in the art to which the present disclosure pertains. All patents and publications are herein incorporated by reference to the same extent as if each individual publication was specifically and individually indicated to be incorporated by reference.

The publications discussed throughout are provided solely for their disclosure before the filing date of the present application. Nothing herein is to be construed as an admission that the invention is not entitled to antedate such disclosure by virtue of prior invention.

The following examples are included to demonstrate the disclosure. It should be appreciated by those of skill in the art that the techniques disclosed in the following examples represent techniques discovered by the inventors to function well in the practice of the disclosure. Those of skill in the art should, however, in light of the present disclosure, appreciate that many changes could be made in the disclosure and still obtain a like or similar result without departing from the spirit and scope of the disclosure, therefore all matter set forth is to be interpreted as illustrative and not in a limiting sense.

Example 1. Adhesive Portion Comprising High Water Content

To prepare the adhesive portion of the animal treat on the bench top in an attempt to approximate thermal extrusion conditions, the dry ingredients are blended together. The wet ingredients are combined separately from the dry ingredients. The dry ingredients are then added to the wet ingredients and the ingredients are mixed until consistent. The mixture is then quickly heated to 195-205° F., placed into a food processor, and processed at high speed for about 40 seconds to simulate "shear" forces similar to those that would be seen in production through extrusion.

In this example, formulations for the adhesive portion of an animal treat of the invention are prepared using a high water content in an attempt to achieve better adhesion to oral medication in the form of a pill. Tables 1-16 depict the ingredients and amounts of the ingredients used to prepare the adhesive portion of the animal treat.

TABLE 1

|  |  | Batch Size 150 g Formula #1 C | |
|---|---|---|---|
|  |  | Wt % | Weight in grams |
| G - | Pregel Rice Flour | 0% | 0 |
|  | Pregel Corn Flour | 10.41% | 15.61 |
|  | Pregel Wheat Flour | 0.00% | 0 |
|  | Pregel Potato | 10.41% | 15.61 |
|  | Gelatin | 0.00% | 0 |
| Palatants | Sweet Potato Powder | 0.00% | 0 |
|  | Black Melted Barley | 0.00% | 0 |
|  | SD Chicken meat | 0.00% | 0 |
|  | AFB Liver Digest | 0.00% | 0 |
|  | AFB Palatant | 0.00% | 0 |
|  | Salt | 0.00% | 0 |
|  | Chicken Digest | 0.00% | 0 |
| Stabilizer | Micro Guard | 1.50% | 2.25 |
|  | Potassium Sorbate |  |  |
| Humectant | Dried Rice Syrup | 0.00% | 0 |
|  | Dried Molasses | 13.25% | 19.87 |
|  | Sugar | 0.00% | 0 |
|  | Dried Rice Syrup | 0.00% | 0 |
|  | Corn Syrup | 23.90% | 35.85 |
|  | Glycerin | 15.30% | 22.95 |
|  | Rice Syrup | 0.00% | 0 |
| Acidifier | Phosphoric Acid | 0.24% | 0.36 |
|  | Acidified Calcium Sulfate |  |  |
| Water | Process water | 25.00% | 37.50 |
|  |  | 100.00% | 150.01 | 0.00 |

TABLE 2

|  |  | Batch Size 150 Formula #2 C | |
|---|---|---|---|
| Glue | Pregel Rice Flour | 12.03% | 18.05 |
| Backbo | Pregel Corn Flour | 0.00% | 0.00 |
|  | Pregel Wheat Flour | 0.00% | 0.00 |
|  | Pregel Potato | 0.00% | 0.00 |
|  | Gelatin | 0.00% | 0.00 |

TABLE 2-continued

|  |  | Batch Size 150 Formula #2 C | | |
|---|---|---|---|---|
| Palatants | Sweet Potato Powder | 0.73% | 1.10 | |
|  | Black Melted Barley | 0.00% | 0.00 | |
|  | SD Chicken meat | 1.57% | 2.36 | |
|  | AFB Liver Digest | 0.20% | 0.30 | |
|  | AFB Palatant | 0.08% | 0.12 | |
|  | Salt | 0.39% | 0.59 | |
|  | Chicken Digest | 4.25% | 6.38 | |
| Stabilizer | Micro Guard | 1.50% | 2.25 | |
|  | Potassium Sorbate | 0.00% | 0.00 | |
| Humectant | Dried Rice Syrup | 0.00% | 0.00 | |
|  | Dried Molasses | 0.00% | 0.00 | |
|  | Sugar | 10.84% | 16.26 | |
|  | Dried Rice Syrup | 15.39% | 23.09 | |
|  | Corn Syrup | 7.85% | 11.78 | |
|  | Glycerin | 12.17% | 18.26 | |
|  | Rice Syrup | 0.00% | 0.00 | |
| Acidifier | Phosphoric Acid |  |  | |
|  | Acidified Calcium Sulfate |  |  | |
| Water | Process water | 33.00% | 49.50 | |
|  |  | 100.00% | 150.01 | 0.00% |

TABLE 3

|  |  | Batch Size 150 Formula #3 C | | |
|---|---|---|---|---|
| Glue Backbone | Pregel Rice Flour | 0.00% | 0.00 | |
|  | Pregel Corn Flour | 14.50% | 21.75 | |
|  | Pregel Wheat Flour | 0.00% | 0.00 | |
|  | Pregel Potato | 0.00% | 0.00 | |
|  | Gelatin | 2.00% | 3.00 | |
| Palat | Sweet Potato Powder | 0.00% | 0.00 | |
|  | Black Melted Barley | 1.00% | 1.59 | |
|  | SD Chicken meat | 1.78% | 2.67 | |
|  | AFB Liver Digest | 0.27% | 0.40 | |
|  | AFB Palatant | 0.12% | 0.18 | |
|  | Salt | 0.48% | 0.71 | |
|  | Chicken Digest | 4.25% | 6.38 | |
| Stabilizer | Micro Guard | 1.50% | 2.25 | |
|  | Potassium Sorbate |  |  | |
| Humectant | Dried Rice Syrup | 2.00% | 3.00 | |
|  | Dried Molasses | 12.53% | 18.80 | |
|  | Sugar | 0.00% | 0.00 | |
|  | Dried Rice Syrup | 0.00% | 0.00 | |
|  | Corn Syrup | 0.00% | 0.00 | |
|  | Glycerin | 13.81% | 20.71 | |
|  | Rice Syrup | 12.65% | 18.97 | |
| Acidfier | Phosphoric Acid | 0.00% |  | |
|  | Acidified Calcium Sulfate | 0.00% |  | |
| Water | Process water | 33.12% | 49.68 | |
|  |  | 100.00% | 149.99 | 0.00 |

TABLE 4

|  |  | Batch Size 150 Formula #4 C | |
|---|---|---|---|
| Glue Backbone | Pregel Rice Flour | 0.00% | 0.00 |
|  | Pregel Corn Flour | 0.00% | 0.00 |
|  | Pregel Wheat Flour | 15.00% | 22.50 |
|  | Pregel Potato | 0.00% | 0.00 |
|  | Gelatin | 1.77% | 2.65 |
| Palatants | Sweet Potato Powder | 0.00% | 0.00 |
|  | Black Melted Barley | 1.00% | 1.50 |
|  | SD Chicken meat | 1.77% | 2.65 |
|  | AFB Liver Digest | 0.00% | 0.00 |
|  | AFB Palatant | 0.00% | 0.00 |
|  | Salt | 0.00% | 0.00 |
|  | Chicken Digest | 5.60% | 8.40 |
| Stabilizer | Micro Guard | 1.50% | 2.25 |
|  | Potassium Sorbate |  |  |

TABLE 4-continued

|  |  | Batch Size 150 Formula #4 C | | |
|---|---|---|---|---|
| Humectant | Dried Rice Syrup | 0.00% | 0.00 | |
|  | Dried Molasses | 0.00% | 0.00 | |
|  | Sugar | 10.00% | 15.00 | |
|  | Dried Rice Syrup | 17.00% | 25.50 | |
|  | Corn Syrup | 8.84% | 13.25 | |
|  | Glycerin | 14.00% | 21.00 | |
|  | Rice Syrup | 0.00% | 0.00 | |
| Acidifier | Phosphoric Acid | 0.00% |  | |
|  | Acidified Calcium Sulfate | 0.00% |  | |
| Water | Process water | 23.53% | 35.30 | |
|  |  | 100.00% | 150.00 | 0.00 |

TABLE 5

|  |  | Batch Size 150 Formula #5 C | | |
|---|---|---|---|---|
| Glue Backbone | Pregel Rice Flour | 0.00% | 0.00 | |
|  | Pregel Corn Flour | 0.00% | 0.00 | |
|  | Pregel Wheat Flour | 0.00% | 0.00 | |
|  | Pregel Potato | 11.72% | 17.58 | |
|  | Gelatin | 1.56% | 2.34 | |
| Palatants | Sweet Potato Powder | 0.20% | 0.30 | |
|  | Black Melted Barley | 1.17% | 1.76 | |
|  | SD Chicken meat | 1.56% | 2.34 | |
|  | AFB Liver Digest | 0.78% | 1.17 | |
|  | AFB Palatant | 0.86% | 1.29 | |
|  | Salt | 0.39% | 0.59 | |
|  | Chicken Digest | 0.00% | 0.00 | |
| Stabilizer | Micro Guard | 1.50% | 2.25 | |
|  | Potassium Sorbate |  |  | |
| Humectant | Dried Rice Syrup | 15.31% | 22.97 | |
|  | Dried Molasses | 10.78% | 16.17 | |
|  | Sugar | 0.00% | 0.00 | |
|  | Dried Rice Syrup | 0.00% | 0.00 | |
|  | Corn Syrup | 0.00% | 0.00 | |
|  | Glycerin | 14.00% | 21.00 | |
|  | Rice Syrup | 5.41% | 8.12 | |
| Acidifier | Phosphoric Acid |  |  | |
|  | Acidified Calcium Sulfate | 0.38% | 0.57 | |
| Water | Process water | 34.37% | 51.56 | |
|  |  | 100.00% | 150.00 | 0.00 |

TABLE 6

|  |  | Batch Size 150 Formula #6 C | |
|---|---|---|---|
| Glue Backbone | Pregel Rice Flour | 0.00% | 0.00 |
|  | Pregel Corn Flour | 0.00% | 0.00 |
|  | Pregel Wheat Flour | 0.00% | 0.00 |
|  | Pregel Potato | 8.00% | 12.00 |
|  | Gelatin | 8.00% | 12.00 |
| Palatants | Sweet Potato Powder | 0.00% | 0.00 |
|  | Black Melted Barley | 1.00% | 1.50 |
|  | SD Chicken meat | 1.80% | 2.70 |
|  | AFB Liver Digest | 0.80% | 1.20 |
|  | AFB Palatant | 0.80% | 1.20 |
|  | Salt | 0.50% | 0.75 |
|  | Chicken Digest | 0.00% | 0.00 |
| Stabili | Micro Guard | 1.50% | 2.25 |
|  | Potassium Sorbate |  |  |
| Humectant | Dried Rice Syrup | 13.35% | 20.03 |
|  | Dried Molasses | 10.00% | 15.00 |
|  | Sugar | 0.00% | 0.00 |
|  | Dried Rice Syrup | 0.00% | 0.00 |
|  | Corn Syrup | 10.00% | 15.00 |
|  | Glycerin | 14.00% | 21.00 |
|  | Rice Syrup | 0.00% | 0.00 |

TABLE 6-continued

Batch Size 150 Formula #6 C

| | | | |
|---|---|---|---|
| Acidifier | Phosphoric Acid | | |
| | Acidified Calcium Sulfate | 0.25% | 0.38 |
| Water | Process water | 30.00% | 45.00 |
| | | 100.00% | 150 |

TABLE 7

Batch Size 150 Formula #1 D

| | | | | |
|---|---|---|---|---|
| Glue | Pregel Rice Flour | 0% | 0 | |
| Backbone | Pregel Corn Flour | 7.25% | 10.88 | |
| | Pregel Wheat Flour | 0.00% | 0 | |
| | Pregel Potato | 7.25% | 10.88 | |
| | Gelatin | 0.00% | 0 | |
| Palatants | Sweet Potato Powder | 0.00% | 0 | |
| | Black Melted Barley | 0.00% | 0 | |
| | SD Chicken meat | 0.00% | 0 | |
| | AFB Liver Digest | 0.00% | 0 | |
| | AFB Palatant | 0.00% | 0 | |
| | Salt | 0.00% | 0 | |
| | Chicken Digest | 0.00% | 0 | |
| Stabilizer | Micro Guard | 1.50% | 2.25 | |
| | Potassium Sorbate | | | |
| Hu | Dried Rice Syrup | 0.00% | 0 | |
| | Dried Molasses | 8.73% | 13.10 | |
| | Sugar | 10.00% | 15.00 | |
| | Dried Corn Syrup | 15.39% | 23.00 | |
| | Corn Syrup | 7.33% | 11.00 | |
| | Glycerin | 12.17% | 18.26 | |
| | Rice Syrup | 0.00% | 0 | |
| Acidifier | Phosphoric Acid | | | |
| | Acidified Calcium Sulfate | 0.38% | 0.57 | |
| Water | Process water | 30.00% | 45.00 | |
| | | 100.00% | 150.01 | 0.00 |

TABLE 8

Batch Size 150 Formula #1 E

| | | | | |
|---|---|---|---|---|
| Glue | Pregel Rice Flour | 0% | 0 | |
| Backbone | Pregel Corn Flour | 7.25% | 10.88 | |
| | Pregel Wheat Flour | 0.00% | 0 | |
| | Pregel Potato | 7.25% | 10.88 | |
| | Gelatin | 0.00% | 0 | |
| Palatants | Sweet Potato Powder | 0.00% | 0 | |
| | Black Melted Barley | 0.00% | 0 | |
| | SD Chicken meat | 0.00% | 0 | |
| | AFB Liver Digest | 0.00% | 0 | |
| | AFB Palatant | 0.00% | 0 | |
| | Salt | 0.00% | 0 | |
| | Chicken Digest | 0.00% | 0 | |
| Stabilizer | Micro Guard | 1.50% | 2.25 | |
| | Potassium Sorbate | | | |
| Humectant | Dried Rice Syrup | 0.00% | 0.00 | |
| | Dried Molasses | 11.00% | 16.50 | |
| | Sugar | 0.00% | 0.00 | |
| | Dried Rice Syrup | 15.40% | 23.10 | |
| | Corn Syrup | 0.00% | 0.00 | |
| | Glycerin | 12.20% | 18.30 | |
| | Rice Syrup | 15.00% | 22.50 | |
| Acidifier | Phosphoric Acid | | | |
| | Acidified Calcium Sulfate | 0.40% | 0.60 | |
| Water | Process water | 30.00% | 45.00 | |
| | | 100.00% | 150.00 | 0.00 |

TABLE 9a

Batch Size 150 Formula #2 E

| | | | | |
|---|---|---|---|---|
| Glue | Pregel Rice Flour | 14.50% | 21.75 | |
| Backbone | Pregel Corn Flour | 0.00% | 0.00 | |
| | Pregel Wheat Flour | 0.00% | 0.00 | |
| | Pregel Potato | 0.00% | 0.00 | |
| | Gelatin | 0.00% | 0.00 | |
| Palatants | Sweet Potato Powder | 0.00% | 0.00 | |
| | Black Melted Barley | 0.00% | 0.00 | |
| | SD Chicken meat | 0.00% | 0.00 | |
| | AFB Liver Digest | 0.00% | 0.00 | |
| | AFB Palatant | 0.00% | 0.00 | |
| | Salt | 0.00% | 0.00 | |
| | Chicken Digest | 0.00% | 0.00 | |
| Stabilizer | Micro Guard | 1.50% | 2.25 | |
| | Potassium Sorbate | | | |
| Humectant | Dried Rice Syrup | 0.00% | 0.00 | |
| | Dried Molasses | 11.00% | 16.50 | |
| | Sugar | 0.00% | 0.00 | |
| | Dried Rice Syrup | 15.40% | 23.10 | |
| | Corn Syrup | 0.00% | 0.00 | |
| | Glycerin | 12.20% | 18.30 | |
| | Rice Syrup | 15.00% | 22.50 | |
| Acidifier | Phosphoric Acid | | | |
| | Acidified Calcium Sulfate | 0.40% | 0.60 | |
| Water | Process water | 30.00% | 45.00 | |
| | | 100.00% | 150.00 | 0.00% |

TABLE 9b

Batch Size 150 Formula #1 F

| | | | | |
|---|---|---|---|---|
| Glue | Pregel Rice Flour | 0% | 0 | |
| Backbone | Pregel Corn Flour | 8.00% | 12.00 | |
| | Pregel Wheat Flour | 0.00% | 0 | |
| | Pregel Potato | 8.00% | 12.00 | |
| | Gelatin | 0.00% | 0 | |
| Palatants | Sweet Potato Powder | 0.00% | 0 | |
| | Black Melted Barley | 0.00% | 0 | |
| | SD Chicken meat | 0.00% | 0 | |
| | AFB Liver Digest | 0.00% | 0 | |
| | AFB Palatant | 0.00% | 0 | |
| | Salt | 0.00% | 0 | |
| | Chicken Digest | 0.00% | 0 | |
| Stabilizer | Micro Guard | 1.50% | 2.25 | |
| | Potassium Sorbate | | | |
| Humectant | Dried Rice Syrup | 0.00% | 0 | |
| | Dried Molasses | 11.00% | 16.50 | |
| | Sugar | 0.00% | 0.00 | |
| | Dried Rice Syrup | 15.40% | 23.10 | |
| | Corn Syrup | 0.00% | 0.00 | |
| | Glycerin | 12.20% | 18.30 | |
| | Rice Syrup | 16.00% | 24.00 | |
| Acidifier | Phosphoric Acid | | | |
| | Acidified Calcium Sulfate | 0.40% | 0.60 | |
| Water | Process water | 27.50% | 41.25 | |
| | | 100.00% | 150.00 | 0.00 |

TABLE 10

Batch Size 150 Formula #2 F

| | | | |
|---|---|---|---|
| Glue | Pregel Rice Flour | 18.00% | 27.00 |
| Backbone | Pregel Corn Flour | 0.00% | 0.00 |
| | Pregel Wheat Flour | 0.00% | 0.00 |
| | Pregel Potato | 0.00% | 0.00 |
| | Gelatin | 0.00% | 0.00 |
| Palatants | Sweet Potato Powder | 0.00% | 0.00 |
| | Black Melted Barley | 0.00% | 0.00 |
| | SD Chicken meat | 0.00% | 0.00 |
| | AFB Liver Digest | 0.00% | 0.00 |
| | AFB Palatant | 0.00% | 0.00 |

TABLE 10-continued

Batch Size 150 Formula #2 F

| Category | Ingredient | % | Amount | |
|---|---|---|---|---|
| | Salt | 0.00% | 0.00 | |
| | Chicken Digest | 0.00% | 0.00 | |
| Stabilizer | Micro Guard Potassium Sorbate | 1.50% | 2.25 | |
| Humectant | Dried Rice Syrup | 0.00% | 0.00 | |
| | Dried Molasses | 11.00% | 16.50 | |
| | Sugar | 0.00% | 0.00 | |
| | Dried Rice Syrup | 15.40% | 23.10 | |
| | Corn Syrup | 0.00% | 0.00 | |
| | Glycerin | 12.20% | 18.30 | |
| | Rice Syrup | 16.00% | 24.00 | |
| Acidifier | Phosphoric Acid | | | |
| | Acidified Calcium Sulfate | 0.40% | 0.60 | |
| Water | Process water | 25.50% | 38.25 | |
| | | 100.00% | 150.00 | 0.00% |

TABLE 11

Batch Size 150 Formula #3 F

| Category | Ingredient | % | Amount | |
|---|---|---|---|---|
| Glue Backbone | Pregel Rice Flour | 0.00% | 0.00 | |
| | Pregel Corn Flour | 16.00% | 24.00 | |
| | Pregel Wheat Flour | 0.00% | 0.00 | |
| | Pregel Potato | 0.00% | 0.00 | |
| | Gelatin | 0.00% | 0.00 | |
| Palatants | Sweet Potato Powder | 0.00% | 0.00 | |
| | Black Melted Barley | 0.00% | 0.00 | |
| | SD Chicken meat | 0.00% | 0.00 | |
| | AFB Liver Digest | 0.00% | 0.00 | |
| | AFB Palatant | 0.00% | 0.00 | |
| | Salt | 0.00% | 0.00 | |
| | Chicken Digest | 0.00% | 0.00 | |
| Stabilizer | Micro Guard Potassium Sorbate | 1.50% | 2.25 | |
| Humectant | Dried Rice Syrup | 0.00% | 0.00 | |
| | Dried Molasses | 11.00% | 16.50 | |
| | Sugar | 0.00% | 0.00 | |
| | Dried Rice Syrup | 15.40% | 23.10 | |
| | Corn Syrup | 0.00% | 0.00 | |
| | Glycerin | 12.20% | 18.30 | |
| | Rice Syrup | 16.00% | 24.00 | |
| Acidifier | Phosphoric Acid | | | |
| | Acidified Calcium Sulfate | 0.40% | 0.60 | |
| Water | Process water | 27.50% | 41.25 | |
| | | 100.00% | 150.00 | |

TABLE 12

Batch Size 150 Formula #4 F

| Category | Ingredient | % | Amount |
|---|---|---|---|
| Glue Backbone | Pregel Rice Flour | 0.00% | 0.00 |
| | Pregel Corn Flour | 0.00% | 0.00 |
| | Pregel Wheat Flour | 16.00% | 24.00 |
| | Pregel Potato | 0.00% | 0.00 |
| | Gelatin | 0.00% | 0.00 |
| Palatants | Sweet Potato Powder | 0.00% | 0.00 |
| | Black Melted Barley | 0.00% | 0.00 |
| | SD Chicken meat | 0.00% | 0.00 |
| | AFB Liver Digest | 0.00% | 0.00 |
| | AFB Palatant | 0.00% | 0.00 |
| | Salt | 0.00% | 0.00 |
| | Chicken Digest | 0.00% | 0.00 |
| Stabilizer | Micro Guard Potassium Sorbate | 1.50% | 2.25 |
| Humectant | Dried Rice Syrup | 0.00% | 0.00 |
| | Dried Molasses | 11.00% | 16.50 |
| | Sugar | 0.00% | 0.00 |
| | Dried Rice Syrup | 15.40% | 23.10 |
| | Corn Syrup | 0.00% | 0.00 |

TABLE 12-continued

Batch Size 150 Formula #4 F

| Category | Ingredient | % | Amount | |
|---|---|---|---|---|
| | Glycerin | 12.20% | 18.30 | |
| | Rice Syrup | 15.00% | 22.50 | |
| Acidifier | Phosphoric Acid | | | |
| | Acidified Calcium Sulfate | 0.40% | 0.60 | |
| Water | Process water | 25.00% | 37.50 | |
| | | 96.50% | 144.75 | 0.00 |

TABLE 13

Batch Size 150 Formula #5 F

| Category | Ingredient | % | Amount | |
|---|---|---|---|---|
| Glue Backbone | Pregel Rice Flour | 0.00% | 0.00 | |
| | Pregel Corn Flour | 0.00% | 0.00 | |
| | Pregel Wheat Flour | 0.00% | 0.00 | |
| | Pregel Potato | 15.00% | 22.50 | |
| | Gelatin | 0.00% | 0.00 | |
| Palatants | Sweet Potato Powder | 0.00% | 0.00 | |
| | Black Melted Barley | 0.00% | 0.00 | |
| | SD Chicken meat | 0.00% | 0.00 | |
| | AFB Liver Digest | 0.00% | 0.00 | |
| | AFB Palatant | 0.00% | 0.00 | |
| | Salt | 0.00% | 0.00 | |
| | Chicken Digest | 0.00% | 0.00 | |
| Stabilizer | Micro Guard Potassium Sorbate | 1.50% | 2.25 | |
| Humectant | Dried Rice Syrup | 0.00% | 0.00 | |
| | Dried Molasses | 11.00% | 16.50 | |
| | Sugar | 0.00% | 0.00 | |
| | Dried Rice Syrup | 15.40% | 23.10 | |
| | Corn Syrup | 0.00% | 0.00 | |
| | Glycerin | 12.20% | 18.30 | |
| | Rice Syrup | 16.00% | 24.00 | |
| Acidifier | Phosphoric Acid | | | |
| | Acidified Calcium Sulfate | 0.40% | 0.60 | |
| Water | Process water | 28.50% | 42.75 | |
| | | 100.00% | 150.00 | 0.00 |

TABLE 14

Batch Size 150 Formula #1 G

| Category | Ingredient | % | Amount | |
|---|---|---|---|---|
| Glue Backbone | Pregel Rice Flour | 0% | 0 | |
| | Pregel Corn Flour | 6.00% | 9.00 | |
| | Pregel Wheat Flour | 0.00% | 0 | |
| | Pregel Potato | 6.00% | 9.00 | |
| | Gelatin | 1.50% | 0 | |
| Palatants | Sweet Potato Powder | 0.00% | 0 | |
| | Black Melted Barley | 0.00% | 0 | |
| | SD Chicken meat | 0.00% | 0 | |
| | AFB Liver Digest | 0.00% | 0 | |
| | AFB Palatant | 0.00% | 0 | |
| | Salt | 0.00% | 0 | |
| | Chicken Digest | 0.00% | 0 | |
| Stabilizer | Micro Guard Potassium Sorbate | 1.50% | 2.25 | |
| Humectant | Dried Rice Syrup | 0.00% | 0 | |
| | Dried Molasses | 13.40% | 20.10 | |
| | Sugar | 0.00% | 0.00 | |
| | Dried Rice Syrup | 15.40% | 23.10 | |
| | Corn Syrup | 0.00% | 0.00 | |
| | Glycerin | 12.20% | 18.30 | |
| | Rice Syrup | 16.00% | 24.00 | |
| Acidifier | Phosphoric Acid | | | |
| | Acidified Calcium Sulfate | 0.50% | 0.75 | |
| Water | Process water | 27.50% | 41.25 | |
| | | 100.00% | 147.75 | 0.00 |

TABLE 15

| | | Batch Size 150 Formula #2 G | |
|---|---|---|---|
| Glue Backbone | Pregel Rice Flour | 18.00% | 27.00 |
| | Pregel Corn Flour | 0.00% | 0.00 |
| | Pregel Wheat Flour | 0.00% | 0.00 |
| | Pregel Potato | 0.00% | 0.00 |
| | Gelatin | 1.50% | 2.25 |
| Palatants | Sweet Potato Powder | 0.00% | 0.00 |
| | Black Melted Barley | 0.00% | 0.00 |
| | SD Chicken meat | 0.00% | 0.00 |
| | AFB Liver Digest | 0.00% | 0.00 |
| | AFB Palatant | 0.00% | 0.00 |
| | Salt | 0.00% | 0.00 |
| | Chicken Digest | 0.00% | 0.00 |
| Stabilizer | Micro Guard | 1.50% | 2.25 |
| | Potassium Sorbate | | |
| Humectant | Dried Rice Syrup | 0.00% | 0.00 |
| | Dried Molasses | 9.90% | 14.85 |
| | Sugar | 0.00% | 0.00 |
| | Dried Rice Syrup | 15.40% | 23.10 |
| | Corn Syrup | 0.00% | 0.00 |
| | Glycerin | 12.20% | 18.30 |
| | Rice Syrup | 16.00% | 24.00 |
| Acidifier | Phosphoric Acid | | |
| | Acidified Calcium Sulfate | 0.50% | 0.75 |
| Water | Process water | 25.00% | 37.50 |
| | | 100.00% | 150.00  0.00% |

TABLE 16

| | | Batch Size 150 Formula #5 G | |
|---|---|---|---|
| Glue Backbone | Pregel Rice Flour | 0.00% | 0.00 |
| | Pregel Corn Flour | 0.00% | 0.00 |
| | Pregel Wheat Flour | 0.00% | 0.00 |
| | Pregel Potato | 10.00% | 15.00 |
| | Gelatin | 0.00% | 0.00 |
| Palatants | Sweet Potato Powder | 0.00% | 0.00 |
| | Black Melted Barley | 0.00% | 0.00 |
| | SD Chicken meat | 0.00% | 0.00 |
| | AFB Liver Digest | 0.00% | 0.00 |
| | AFB Palatant | 0.00% | 0.00 |
| | Salt | 0.00% | 0.00 |
| | Chicken Digest | 0.00% | 0.00 |
| Stabilizer | Micro Guard | 1.50% | 2.25 |
| | Potassium Sorbate | | |
| Humectant | Dried Rice Syrup | 0.00% | 0.00 |
| | Dried Molasses | 15.90% | 23.85 |
| | Sugar | 0.00% | 0.00 |
| | Dried Rice Syrup | 15.40% | 23.10 |
| | Corn Syrup | 0.00% | 0.00 |
| | Glycerin | 12.20% | 18.30 |
| | Rice Syrup | 16.00% | 24.00 |
| Acidifier | Phosphoric Acid | | |
| | Acidified Calcium Sulfate | 0.50% | 0.75 |
| Water | Process water | 28.50% | 42.75 |
| | | 100.00% | 150.00  0.00 |

Example 2. Preparation and Composition of an Aspect of a Pilling Treat

To prepare the outer portion of the animal treat, a Dry mix, a Slurry, and a Digest are first prepared (Table 17). The Digest is prepared as follows:
Add Chicken Meat to digest preparation tank,
Add Acidified Calcium Sulfate and Water to Digest preparation tank,
Mix until uniform,
Transfer to Slurry Tank,
Heat to 130° F. and hold for 15 minutes.

TABLE 17

| | | | |
|---|---|---|---|
| Batch Size: Dry | | 10 | |
| Batch Size: Slurry | | 5 | |
| Batch Size: Digest | | 6 | |
| Ingredient | % Total | Pounds | |
| Sweet Rice flour | 60.89% | 6.09 | |
| Waxy Maize: | 0.00% | 0.00 | |
| Stabilized Rice Bran | 7.86% | 0.79 | |
| Sweet Potato Powder | 7.86% | 0.79 | |
| Dried Molasses | 0.00% | 0.00 | |
| Gelatin- | 4.72% | 0.47 | |
| SD Chicken meat | 2.75% | 0.28 | |
| AFB Liver Digest | 1.18% | 0.12 | |
| Dried Rice Syrup | 4.72% | 0.47 | |
| Dried Egg Yolk Product | 3.14% | 0.31 | |
| Salt | 0.68% | 0.07 | |
| Micro Guard | 2.75% | 0.28 | |
| AFB Palatant | 0.16% | 0.02 | |
| NaturOx Plus | 0.16% | 0.02 | |
| Black Malted Barley | 0.79% | 0.08 | |
| Poultry Meal | 2.36% | 0.24 | |
| Total | 100.00% | 10.00 | |
| Chicken meat | 36.36% | 1.82 | |
| Glycerin | 36.36% | 1.82 | |
| Rice Syrup 64DE | 27.27% | 1.36 | |
| Total | 100.00% | 5.00 | |
| Chicken | 29.50% | 1.77 | |
| Acidified Calcium Sulfate | 26.25% | 1.58 | |
| Water | 44.25% | 2.65 | |
| Total | 100.00% | 6.00 | |

The "Digest" is made in a Slurry Tank first before batching "Slurry" and "Slurry" is batched on top of "Digest".

TABLE 18

| Dry as % of Formula: | 63.61% | Water as % of dry feed | 17.29% |
|---|---|---|---|
| Slurry as % of Formula: | 22.00% | Slurry as % of dry feed | 34.59% |
| Digest as % of Formula: | 3.39% | | |

The final composition of the outer portion is shown in Table 19.

TABLE 19

| Total | Ingredient | Dry Mix | Slurry | Fresh Digest |
|---|---|---|---|---|
| 38.73% | Sweet Rice flour | 60.89% | | |
| 0.00% | Waxy Maize: | 0.00% | | |
| 5.00% | Stabilized Rice Bran ( | 7.86% | | |
| 5.00% | Sweet Potato Powder | 7.86% | | |
| 0.00% | Dried Molasses | 0.00% | | |
| 3.00% | Gelatin- | 4.72% | | |
| 1.75% | SD Chicken meat | 2.75% | | |
| 0.75% | AFB Liver Digest | 1.18% | | |
| 3.00% | Dried Rice Syrup | 4.72% | | |
| 2.00% | Dried Egg Yolk Product | 3.14% | | |
| 0.43% | Salt | 0.68% | | |
| 1.75% | Micro Guard | 2.75% | | |
| 0.10% | AFB Palatant | 0.16% | | |
| 0.10% | NaturOx Plus | 0.16% | | |
| 0.50% | Black Malted Barley | 0.79% | | |
| 1.50% | Poultry Meal | 2.36% | | |
| 0.00% | | 0.00% | | |

TABLE 19-continued

| Total | Ingredient | Dry Mix | Slurry | Fresh Digest |
|---|---|---|---|---|
| 8.00% | Chicken meat | | 36.36% | |
| 8.00% | Glycerin | | 36.36% | |
| 6.00% | Rice Syrup 64DE | | 27.27% | |
| 1.00% | Chicken | | | 29.50% |
| 0.89% | Acidified Calcium Sulfate | | | 26.25% |
| 1.50% | Water | | | 44.25% |
| 11.00% | Process Water | | | |
| | | 100.0% | 100.00% | 100.00% |
| 100.00% | | 63.61% | 22.000% | 3.39% |

To prepare the adhesive portion of the animal treat, a Dry mix, a Slurry, and a Digest are first prepared (Table 20). The Digest is prepared as follows:
Add Chicken Meat to digest preparation tank,
Add Acidified Calcium Sulfate and Water to Digest preparation tank,
Mix until uniform,
Transfer to Slurry Tank,
Heat to 130° F. and hold for 15 minutes.

The "Digest" is made in a Slurry Tank first before batching "Slurry" and "Slurry" is batched on top of "Digest".

TABLE 20

| Batch Size: Dry | 10 |
|---|---|
| Batch Size: Slurry | 5 |
| Batch Size: Fresh Digest | 6 |

| Ingredient | % Total | Pounds |
|---|---|---|
| Sweet Rice flour | 12.16% | 1.22 |
| Waxy Maize: | 31.66% | 3.17 |
| Stabilized Rice Bran | 0.00% | 0.00 |
| Sweet Potato Powder | 0.00% | 0.00 |
| Dried Molasses | 28.59% | 2.86 |
| Gelatin- | 3.65% | 0.36 |
| SD Chicken meat | 4.86% | 0.49 |
| AFB Liver Digest Optimizor | 0.61% | 0.06 |
| Dried Rice Syrup 42DE | 9.73% | 0.97 |
| Dried Egg Yolk Product | 0.00% | 0.00 |
| Salt | 1.22% | 0.12 |
| Micro Guard | 3.65% | 0.36 |
| AFB Palatant | 3.65% | 0.36 |
| NaturOx Plus | 0.24% | 0.02 |
| Black Malted Barley | 0.00% | 0.00 |
| | 0.00% | 0.00 |
| Total | 100.00% | 10.00 |
| Chicken meat | 16.22% | 0.811 |
| Glycerin | 43.24% | 2.162 |
| Rice Syrup | 40.54% | 2.027 |
| Total | 100.00% | 5.000 |
| Chicken | 34.60% | 2.076 |
| Acidified Calcium Sulfate | 30.10% | 1.806 |
| Water | 34.60% | 2.076 |
| Total | 99.31% | 5.958 |

The "Digest" is made in a Slurry Tank first before batching "Slurry" and "Slurry" is batched on top of "Digest".

TABLE 21

| Dry as % of Formula: | 41.13% | Water as % of dry feed | 46.19% |
|---|---|---|---|
| Slurry as % of Formula: | 37.00% | Slurry as % of dry feed | 89.96% |

TABLE 21-continued

| Fresh Digest as % of Formula: | 2.89% |
|---|---|

The final composition of the adhesive portion is shown in Table 22.

TABLE 22

| Total | Ingredient | Dry Mix | Slurry | Digest |
|---|---|---|---|---|
| 5.00% | Sweet Rice flour | 12.16% | | |
| 13.02% | Waxy Maize: | 31.66% | | |
| 0.00% | Stabilized Rice Bran | 0.00% | | |
| 0.00% | Sweet Potato Powder | 0.00% | | |
| 11.76% | Dried Molasses | 28.59% | | |
| 1.50% | Gelatin- | 3.65% | | |
| 2.00% | SD Chicken meat | 4.86% | | |
| 0.25% | AFB Liver Digest Optimizor | 0.61% | | |
| 4.00% | Dried Rice Syrup | 9.73% | | |
| 0.00% | Dried Egg Yolk Product | 0.00% | | |
| 0.50% | Salt | 1.22% | | |
| 1.50% | Micro Guard | 3.65% | | |
| 1.50% | AFB Palatant | 3.65% | | |
| 0.10% | NaturOx Plus | 0.24% | | |
| 0.00% | Black Malted Barley | 0.00% | | |
| 0.00% | Poultry Meal | 0.00% | | |
| 0.00% | | 0.00% | | |
| 6.00% | Chicken meat | | 16.22% | |
| 16.00% | Glycerin | | 43.24% | |
| 15.00% | Rice Syrup | | 40.54% | |
| 1.00% | Chicken | | | 34.60% |
| 0.87% | Acidified Calcium Sulfate | | | 30.10% |
| 1.00% | Water | | | 34.60% |
| | 0 | | | |
| 19.00% | Process Water | | | |
| | 0 | | | |
| 100.00% | | 100.0% | 100.0% | 99.31% |
| | | 41.13% | 37.00% | 2.87% |

Example 3. Preparation and Composition of an Aspect of a Pilling Treat

To prepare the outer portion of the animal treat, a Dry mix, a Slurry, and a Digest are first prepared (Table 23). The Digest is prepared as follows:
Add Simmons Chicken Meat to digest preparation tank,
Add Acidified Calcium Sulfate and Water to Digest preparation tank,
Mix until uniform,
Transfer to Slurry Tank,
Heat to 130° F. and hold for 15 minutes.

TABLE 23

| Batch Size: Dry | 10 |
|---|---|
| Batch Size: Slurry | 5 |
| Batch Size: Digest | 6 |

| Ingredient | % Total | Pounds |
|---|---|---|
| Sweet Rice flour | 56.93% | 5.69 |
| Waxy Maize | 0.00% | 0.00 |
| Stabilized Rice Bran | 8.83% | 0.88 |
| Sweet Potato Powder | 8.83% | 0.88 |
| Dried Molasses | 0.00% | 0.00 |
| Gelatin- | 3.53% | 0.35 |
| SD Chicken meat | 3.97% | 0.40 |
| AFB Liver Digest Optimizor | 1.32% | 0.13 |
| Dried Rice Syrup | 5.30% | 0.53 |
| Dried Egg Yolk Product | 3.53% | 0.35 |
| Salt | 0.76% | 0.08 |
| Micro Guard | 3.09% | 0.31 |

TABLE 23-continued

| | | |
|---|---|---|
| AFB Palatant | 0.18% | 0.02 |
| NaturOx Plus | 0.18% | 0.02 |
| Black Malted Barley | 0.88% | 0.09 |
| Poultry Meal | 2.65% | 0.26 |
| Total | 100.00% | 10.00 |
| Chicken meat | 33.33% | 1.67 |
| Glycerin | 41.67% | 2.08 |
| Rice Syrup | 25.00% | 1.25 |
| Total | 100.00% | 5.00 |
| Chicken | 29.50% | 1.77 |
| Acidified Calcium Sulfate | 29.50% | 1.77 |
| Water | 41.00% | 2.46 |
| Total | 100.00% | 6.00 |

The "Digest" is made in a Slurry Tank first before batching "Slurry" and "Slurry" is batched on top of "Digest".

TABLE 24

| | | | |
|---|---|---|---|
| Dry as % of Formula: | 56.61% | Water as % of dry feed | 28.26% |
| Slurry as % of Formula: | 24.00% | Slurry as % of dry feed | 42.40% |
| Digest as % of Formula: | 3.39% | | |

The final composition of the outer portion is shown in Table 25.

TABLE 25

| Total | Ingredient | Dry Mix | Slurry | Fresh Digest |
|---|---|---|---|---|
| 32.23% | Sweet Rice flour | 56.93% | | |
| 0.00% | Waxy Maize | 0.00% | | |
| 5.00% | Stabilized Rice Bran | 8.83% | | |
| 5.00% | Sweet Potato Powder | 8.83% | | |
| 0.00% | Dried Molasses | 0.00% | | |
| 2.00% | Gelatin | 3.53% | | |
| 2.25% | SD Chicken meat | 3.97% | | |
| 0.75% | AFB Liver Digest Optimizor B21029 | 1.32% | | |
| 3.00% | Dried Rice Syrup | 5.30% | | |
| 2.00% | Dried Egg yolk product | 3.53% | | |
| 0.43% | Salt | 0.76% | | |
| 1.75% | Micro Guard | 3.09% | | |
| 0.10% | AFB Palatant | 0.18% | | |
| 0.10% | NaturOx Plus | 0.18% | | |
| 0.50% | Black Malted Barley | 0.88% | | |
| 1.50% | Poultry Meal | 2.65% | | |
| 0.00% | | 0.00% | | |
| 8.00% | Chicken meat | | 33.33% | |
| 10.00% | Glycerin | | 41.67% | |
| 6.00% | Rice Syrup | | 25.00% | |
| 1.00% | Chicken | | | 29.50% |
| 1.00% | Acidified Calcium Sulfate | | | 29.50% |
| 1.39% | Water | | | 41.00% |
| 16.00% | Process Water | | | |
| | | 100.0% | 100.00% | 100.00% |
| 100.00% | | 56.61% | 24.000% | 3.39% |

To prepare the adhesive portion of the animal treat, a Dry mix, a Slurry, and a Digest are first prepared (Table 26). The digest is prepared as follows:
Add Chicken Meat to digest preparation tank,
Add Acidified Calcium Sulfate and Water to Digest preparation tank,
Mix until uniform,
Transfer to Slurry Tank,
Heat to 130° F. and hold for 15 minutes.

The "Digest" is made in a Slurry Tank first before batching "Slurry" and "Slurry" is batched on top of "Digest".

TABLE 26

| | | |
|---|---|---|
| Batch Size: Dry | | 10 |
| Batch Size: Slurry | | 5 |
| Batch Size: Fresh Digest | | 6 |
| Ingredient | % Total | Pounds |
| Sweet Rice flour | 8.37% | 0.84 |
| Waxy Maize | 33.47% | 3.35 |
| Stabilized Rice Bran | 0.00% | 0.00 |
| Sweet Potato Powder | 0.00% | 0.00 |
| Dried Molasses | 27.89% | 2.79 |
| Gelatin- | 2.79% | 0.28 |
| SD Chicken meat | 5.58% | 0.56 |
| AFB Liver Digest Optimizor | 0.70% | 0.07 |
| Dried Rice Syrup | 11.16% | 1.12 |
| Dried Egg Yolk Product | 0.00% | 0.00 |
| Salt | 1.39% | 0.14 |
| Micro Guard | 4.18% | 0.42 |
| AFB Palatant | 4.18% | 0.42 |
| NaturOx Plus | 0.28% | 0.03 |
| Black Malted Barley | 0.00% | 0.00 |
| | 0.00% | 0.00 |
| Total | 100.00% | 10.00 |
| Chicken meat | 16.67% | 0.833 |
| Glycerin | 44.44% | 2.222 |
| Rice Syrup 64DE | 38.89% | 1.944 |
| Total | 100.00% | 5.000 |
| Chicken | 34.48% | 2.069 |
| Acidified Calcium Sulfate | 34.48% | 2.069 |
| Water | 31.03% | 1.862 |
| Total | 100.00% | 6.000 |

The "Digest" is made in a Slurry Tank first before batching "Slurry" and "Slurry" is batched on top of "Digest".

TABLE 27

| | | | |
|---|---|---|---|
| Dry as % of Formula: | 35.85% | Water as % of dry feed | 70.43% |
| Slurry as % of Formula: | 36.00% | Slurry as % of dry feed | 100.42% |
| Fresh Digest as % of Formula: | 2.90% | | |

The final composition of the adhesive portion is shown in Table 28.

TABLE 28

| Total | Ingredient | Dry Mix | Slurry | Digest |
|---|---|---|---|---|
| 3.00% | Sweet Rice flour | 8.37% | | |
| 12.00% | Waxy Maize | 33.47% | | |
| 0.00% | Stabilized Rice Bran | 0.00% | | |
| 0.00% | Sweet Potato Powder | 0.00% | | |
| 10.00% | Dried Molasses | 27.89% | | |
| 1.00% | Gelatin- | 2.79% | | |
| 2.00% | SD Chicken meat | 5.58% | | |
| 0.25% | AFB Liver Digest Optimizor | 0.70% | | |
| 4.00% | Dried Rice Syrup | 11.16% | | |
| 0.00% | Dried Egg Yolk Product | 0.00% | | |
| 0.50% | Salt | 1.39% | | |
| 1.50% | Micro Guard | 4.18% | | |
| 1.50% | AFB Palatant | 4.18% | | |
| 0.10% | NaturOx Plus | 0.28% | | |
| 0.00% | Black Malted Barley | 0.00% | | |

TABLE 28-continued

| Total | Ingredient | Dry Mix | Slurry | Digest |
|---|---|---|---|---|
| 0.00% | Poultry Meal | 0.00% | | |
| 0.00% | | 0.00% | | |
| 6.00% | | | 16.67% | |
| 16.00% | Glycerin | | 44.44% | |
| 14.00% | Rice Syrup | | 38.89% | |
| 1.00% | Chicken | | | 34.48% |
| 1.00% | Acidified Calcium Sulfate | | | 34.48% |
| 0.90% | Water | | | 31.03% |
| 25.25% | Process Water | | | |
| 100.00% | | 100.00% | 100.00% | 100.00% |
| | | 35.85% | 36.00% | 2.90% |

Example 4. Preparation and Composition of an Aspect of a Pilling Treat

To prepare the outer portion of the animal treat, a Dry mix, a Slurry, and a Digest are first prepared (Table 29). The Digest is prepared as follows:

Add Chicken Meat to digest preparation tank,

Add Acidified Calcium Sulfate and Water to Digest preparation tank,

Mix until uniform,

Transfer to Slurry Tank,

Heat to 130° F. and hold for 15 minutes.

TABLE 29

Batch Size: Dry 10
Batch Size: Dry 5
Batch Size: Dry 6

| Ingredient | % Total | Pounds |
|---|---|---|
| Sweet Rice flour | 55.95% | 5.59 |
| Waxy Maize | 0.00% | 0.00 |
| Stabilized Rice Bran | 10.41% | 1.04 |
| Sweet Potato Powder | 8.68% | 0.87 |
| Dried Molasses | 0.00% | 0.00 |
| Gelatin- | 3.47% | 0.35 |
| SD Chicken meat | 3.91% | 0.39 |
| AFB Liver Digest Optimizor | 1.30% | 0.13 |
| Dried Rice Syrup 42DE | 5.21% | 0.52 |
| Dried Egg Yolk Product | 3.47% | 0.35 |
| Salt | 0.75% | 0.07 |
| Micro Guard | 3.04% | 0.30 |
| AFB Palatant | 0.17% | 0.02 |
| NaturOx Plus | 0.17% | 0.02 |
| Black Malted Barley | 0.87% | 0.09 |
| Poultry Meal | 2.60% | 0.26 |
| Total | 100.00% | 10.00 |
| Pro-Temp Stabilized Chicken meat (Natural version) | 33.33% | 1.67 |
| Glycerin | 41.67% | 2.08 |
| Rice Syrup 64DE | 25.00% | 1.25 |
| Total | 100.00% | 5.00 |
| Chicken | 29.50% | 1.77 |
| Acidified Calcium Sulfate | 29.50% | 1.77 |
| Water | 41.00% | 2.46 |
| Total | 100.00% | 6.00 |

The "Digest" is made in a Slurry Tank first before batching "Slurry" and "Slurry" is batched on top of "Digest".

TABLE 30

| Dry as % of Formula: | 57.61% | Water as % of dry feed | 26.04% |
|---|---|---|---|
| Slurry as % of Formula: | 24.00% | Slurry as % of dry feed | 41.66% |
| Digest as % of Formula: | 3.39% | | |

The final composition of the outer portion is shown in Table 31.

TABLE 31

| Total | Ingredient | Ingredient No. | Dry Mix | Slurry | Fresh Digest |
|---|---|---|---|---|---|
| 32.23% | Sweet Rice flour | | 55.95% | | |
| 0.00% | Waxy Maize | | 0.00% | | |
| 6.00% | Stabilized Rice Bran | | 10.41% | | |
| 5.00% | Sweet Potato Powder | | 8.68% | | |
| 0.00% | Dried Molasses | | 0.00% | | |
| 2.00% | Gelatin- | | 3.47% | | |
| 2.25% | SD Chicken meat | | 3.91% | | |
| 0.75% | AFB Liver Digest Optimizor | | 1.30% | | |
| 3.00% | Dried Rice Syrup 42DE | | 5.21% | | |
| 2.00% | Dried Egg Yolk Product | | 3.47% | | |
| 0.43% | Salt | | 0.75% | | |
| 1.75% | Micro Guard | | 3.04% | | |
| 0.10% | AFBPalatant | | 0.17% | | |
| 0.10% | NaturOx Plus | | 0.17% | | |
| 0.50% | Black Malted Barley | | 0.87% | | |
| 1.50% | Poultry Meal | | 2.60% | | |
| 0.00% | | | 0.00% | | |
| 8.00% | Chicken meat | | | 33.33% | |
| 10.00% | Glycerin | | | 41.67% | |
| 6.00% | Rice Syrup | | | 25.00% | |
| 1.00% | |Chicken | | | | 29.50% |
| 1.00% | |Acidified Calcium Sulfate | | | | 29.50% |
| 1.39% | |Water | | | | 41.00% |
| 15.00% | Process Water | | | | |
| 100.00% | | | 100.0% | 100.00% | 100.00% |
| | | | 57.61% | 24.000% | 3.39% |

To prepare the adhesive portion of the animal treat, a Dry mix, a Slurry, and a Digest are first prepared (Table 32). The digest is prepared as follows:

Add Chicken Meat to digest preparation tank,

Add Acidified Calcium Sulfate and Water to Digest preparation tank,

Mix until uniform,

Transfer to Slurry Tank,

Heat to 130° F. and hold for 15 minutes.

The "Digest" is made in a Slurry Tank first before batching "Slurry" and "Slurry" is batched on top of "Digest".

TABLE 32

Batch Size: Dry 10
Batch Size: Slurry 5
Batch Size: Fresh Digest 6

| Ingredient | % Total | Pounds |
|---|---|---|
| Sweet Rice flour | 8.14% | 0.81 |
| Waxy Maize | 35.28% | 3.53 |
| Stabilized Rice Bran | 0.00% | 0.00 |
| Sweet Potato Powder | 0.00% | 0.00 |
| Dried Molasses | 27.14% | 2.71 |
| Gelatin- | 2.71% | 0.27 |
| SD Chicken meat | 5.43% | 0.54 |
| AFB Liver Digest Optimizor | 0.68% | 0.07 |
| Dried Rice Syrup 42DE | 10.85% | 1.09 |
| Dried Egg Yolk Product | 0.00% | 0.00 |
| Salt | 1.36% | 0.14 |

TABLE 32-continued

Batch Size: Dry 10
Batch Size: Slurry 5
Batch Size: Fresh Digest 6

| Ingredient | % Total | Pounds |
|---|---|---|
| Micro Guard | 4.07% | 0.41 |
| AFB Palatant | 4.07% | 0.41 |
| NaturOx Plus | 0.27% | 0.03 |
| Black Malted Barley | 0.00% | 0.00 |
|  | 0.00% | 0.00 |
| Total | 100.00% | 10.00 |
| Chicken meat | 16.67% | 0.833 |
| Glycerin | 44.44% | 2.222 |
| Rice Syrup | 38.89% | 1.944 |
| Total | 100.00% | 5.000 |
| Chicken | 34.48% | 2.069 |
| Acidified Calcium Sulfate | 34.48% | 2.069 |
| Water | 31.03% | 1.862 |
| Total | 100.00% | 6.000 |

The "Digest" is made in a Slurry Tank first before batching "Slurry" and "Slurry" is batched on top of "Digest".

TABLE 33

| Dry as % of Formula: | 36.85% | Water as % of dry feed | 65.81% |
|---|---|---|---|
| Slurry as % of Formula: | 36.00% | | |
| Fresh Digest as % of Formula: | 2.90% | Slurry as % of dry feed | 97.69% |

The composition of the adhesive portion is shown in Table 34.

TABLE 34

| Total | Ingredient | Dry Mix | Slurry | Digest |
|---|---|---|---|---|
| 3.00% | Sweet Rice flour | 8.14% | | |
| 13.00% | Waxy Maize | 35.28% | | |
| 0.00% | Stabilized Rice Bran | 0.00% | | |
| 0.00% | Sweet Potato Powder | 0.00% | | |
| 10.00% | Dried Molasses | 27.14% | | |
| 1.00% | Gelatin- | 2.71% | | |
| 2.00% | SD Chicken meat | 5.43% | | |
| 0.25% | AFB Liver Digest Optimizor | 0.68% | | |
| 4.00% | Dried Rice Syrup | 10.85% | | |
| 0.00% | Dried Egg Yolk Product | 0.00% | | |
| 0.50% | Salt | 1.36% | | |
| 1.50% | Micro Guard | 4.07% | | |
| 1.50% | AFB Palatant | 4.07% | | |
| 0.10% | NaturOx Plus | 0.27% | | |
| 0.00% | Black Malted Barley | 0.00% | | |
| 0.00% | Poultry Meal | 0.00% | | |
| 0.00% | | 0.00% | | |
| 6.00% | | | 16.67% | |
| 16.00% | Glycerin | | 44.44% | |
| 14.00% | Rice Syrup | | 38.89% | |
| 1.00% | Chicken | | | 34.48% |
| 1.00% | Acidified Calcium Sulfate | | | 34.48% |
| 0.90% | Water | | | 31.03% |
| 24.25% | Process Water | | | |
| 100.00% | | 100.00% | 100.00% | 100.00% |
| | | 36.85% | 36.00% | 2.90% |

Example 5. Composition of an Aspect of Flavor Bits

Flavor bits are used as particulate material to be delivered to the treat during production. The particulate material can be used to coat adhesive parts exposed during preparation of the treat. The composition of the flavor bits can be as shown in Table 35.

In some aspects, the flavor bits are prepared by extruding the composition. A production die that can be used for this product comprises a 1.5 mm round hole. The product can be slightly expanded off the die when extruded. The slight expansion can ease in reducing size through hammer mill. A final length of the product can be 0.5 mm.

TABLE 35

| Total | Ingredient | Dry Mix | Slurry | Fresh Digest |
|---|---|---|---|---|
| 21.93% | Brown Rice Flour | 28.66% | | |
| 6.00% | sweet potato flour | 7.84% | | |
| 7.00% | Whole Oat Flour | 9.15% | | |
| 10.00% | Pea Starch-pregelatinized | 13.07% | | |
| 10.00% | Pregelatinized Potato Starch | 13.07% | | |
| 2.00% | Spray Dried Chicken | 2.61% | | |
| 2.00% | Poultry Meal | 2.61% | | |
| 1.75% | MicrGard 100 | 2.29% | | |
| 5.00% | Brown Sugar | 6.53% | | |
| 5.00% | Dried Molasses Cane Juice | 6.53% | | |
| 2.00% | Gelatin, | 2.61% | | |
| 1.00% | Egg Product: | 1.31% | | |
| 0.50% | Salt | 0.65% | | |
| 2.25% | Flax Seed Meal | 2.94% | | |
| 0.10% | Nature Ox Plus | 0.13% | | |
| 0.00% | | 0.00% | | |
| 0.00% | | 0.00% | | |
| 0.00% | | 0.00% | | |
| 0.00% | | 0.00% | | |
| 2.00% | Brown Rice Syrup | | 13.11% | |
| 0.25% | Liquid Smoke, | | 1.64% | |
| 1.00% | water | | 6.56% | |
| 12.00% | Glycerin | | 78.69% | |
| 0.00% | | | 0.00% | |
| 1.00% | Chicken | | | 31.06% |
| 0.80% | Acidified Calcium Sulfate | | | 24.84% |
| 1.42% | Water | | | 44.10% |
| 5.00% | Process Water | | | |
| 100.00% | | 100.00% | 100.00% | 100.00% |
| | | 76.53% | 15.25% | 3.22% |

TABLE 36

| Dry as % of Formula: | 76.53% | Water as % of dry feed | 6.533% |
|---|---|---|---|
| Slurry as % of Formula: | 15.25% | Slurry as % of dry feed | 19.93% |
| Fresh Digest as % of Formula: | 3.22% | | |

Example 6. Strength of the Adhesive Portion

Figure 12:
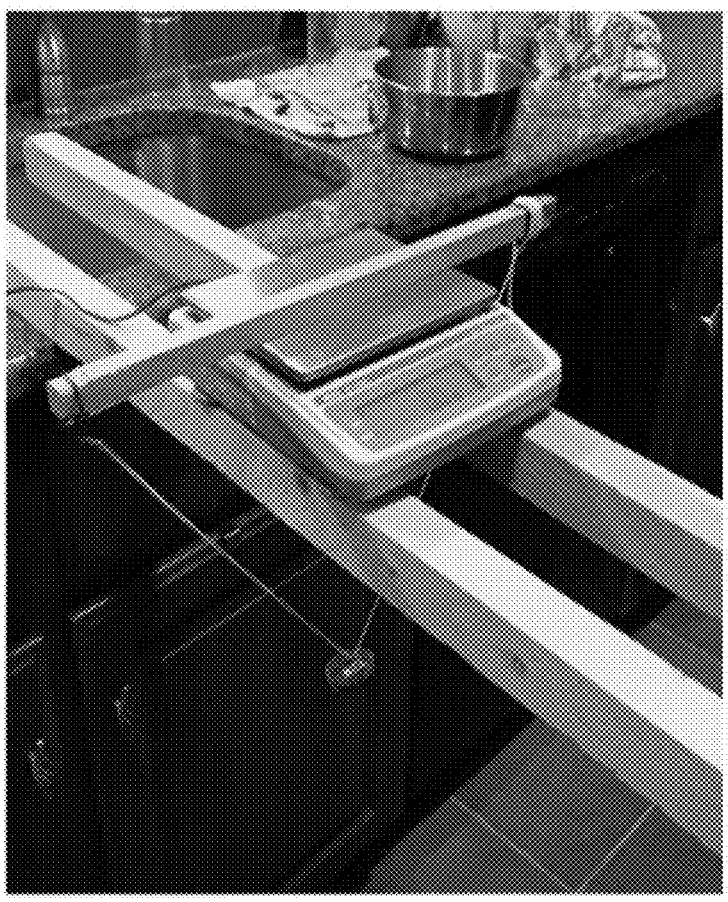
FIG. 12 is a photograph of an anchored tablet pressed into a sample and attached to the scale apparatus shown in FIG. 10.

The strength ("cling") of the adhesive portion was measured using a method comprising the steps of:

1) Filling a sample cup (1.5" diameter Water Activity sample cup) half way with sample adhesive to be tested (FIG. 12).

Figure 11:
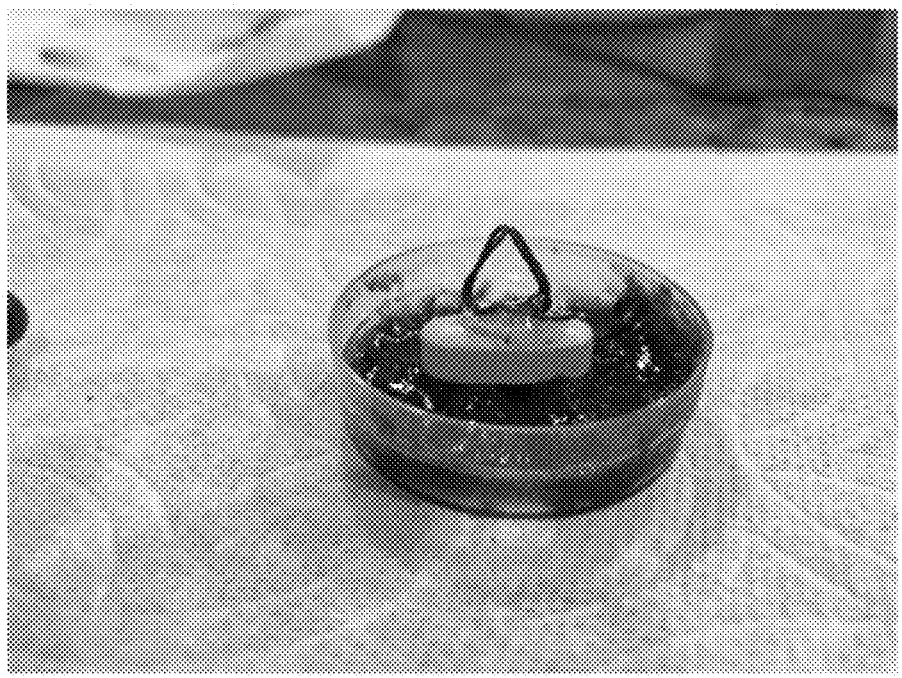
FIG. 11 is a photograph of an anchored tablet pressed onto the adhesive portion.

2) Pressing a medication tablet having an anchor attached thereon into the adhesive to assure sample is solidly filling the cup (FIG. 11), and covering the container and let stand for 8 to 24 hrs.
3) Pre-weighing a control tablet with anchor attachment and documenting the starting weight of the tablet.
4) Uncovering the sample cup and adhering the anchored tablet by pressing only the face of the anchored tablet into the sample to be tested. The tablet does not penetrate the sample below the face of the tablet.
5) Loading the adhered tablet onto the scale apparatus by threading the string through the anchor attachment
6) Slowly pulling down on the sample cup while watching the force exerted on scale until the tablet detaches from the sample. The maximum force exerted to detach the tablet is noted.
7) Documenting the maximum force exerted on the scale to detach the tablet.
8) Weighing the tablet with the sample residue that remained on the tablet and document weight.
9) Verifying the starting weight of the tablet by wiping off adhesive residue and weighing the cleaned tablet. Wipe the tablet and verify the starting weight of the tablet has returned and is free of any sample
10) Repeating steps 4 through 7 two more times, documenting weights after each removal from sample.

The results obtained using this method and multiple samples of the adhesive portion are shown in Table 37. Control adhesives from commercially available pilling treats were also measured. The results clearly show the cling of the adhesive portion when compared to the cling of the control adhesives. In essence, none of the control adhesives were capable of attaching to tablets. The physical characteristic of each control adhesive and various samples of the adhesive portion of the instant disclosure are shown in Table 38.

TABLE 37

Pilling treat cling test showing treat material retained on adhesive portions

| Oval Caplet Tablet used for test | Before pressing into Pill Treat | After pulling out of Pill Treat | | | Average wt after | Treat Material Retained on Pill | % of tablet weight gain |
|---|---|---|---|---|---|---|---|
| | | 1 | 2 | 3 | | | |
| Vet IQ Pilling Treat | 1.52 | 1.52 | 1.52 | 1.52 | 1.5200 | 0.0000 | 0.00% |
| Pill Pocket Duck & Pea flavor | 1.52 | 1.52 | 1.52 | 1.52 | 1.52 | 0.0000 | 0.00% |
| Pill Pocket Hickory Smoke Flavor | 1.52 | 1.52 | 1.52 | 1.52 | 1.52 | 0.0000 | 0.00% |
| Milk Bone Pill Pouch (Chicken) | 1.52 | 1.52 | 1.52 | 1.52 | 1.52 | 0.0000 | 0.00% |
| Vets + Choice Pill Treats (Peanut) | 1.52 | 1.52 | 1.52 | 1.52 | 1.52 | 0.0000 | 0.00% |
| Sample 2C | 1.59 | 1.79 | 1.81 | 1.89 | 1.83 | 0.2400 | 15.1% |
| Sample 3C | 1.61 | 1.68 | 1.66 | 1.7 | 1.68 | 0.0700 | 4.3% |
| Sample 5C | 1.6 | 1.68 | 1.76 | 1.69 | 1.71 | 0.1100 | 6.9% |
| Sample. 6C | 1.53 | 1.54 | 1.54 | 1.55 | 1.54 | 0.0133 | 0.9% |
| Sample. 1D | 1.52 | 1.55 | 1.56 | 1.59 | 1.57 | 0.0467 | 3.1% |
| Sample. 1E | 1.53 | 1.71 | 1.65 | 1.64 | 1.67 | 0.1367 | 8.9% |
| Sample 2E | 1.52 | 1.65 | 1.77 | 1.73 | 1.72 | 0.1967 | 12.9% |
| Sample. 1F | 1.61 | 1.7 | 1.65 | 1.73 | 1.69 | 0.0833 | 5.2% |
| Sample. 2F | 1.6 | 1.75 | 1.84 | 1.85 | 1.81 | 0.2133 | 13.3% |
| Sample. 3F | 1.6 | 1.68 | 1.7 | 1.69 | 1.69 | 0.0900 | 5.6% |
| Sample. 4F | 1.61 | 1.8 | 1.76 | 1.9 | 1.82 | 0.2100 | 13.0% |
| Sample. 5F | 1.53 | 1.63 | 1.65 | 1.69 | 1.66 | 0.1267 | 8.3% |
| Sample 1G | 1.67 | 1.76 | 1.81 | 1.77 | 1.78 | 0.1100 | 6.6% |
| Sample. 2G | 1.67 | 1.88 | 1.85 | 1.9 | 1.88 | 0.2067 | 12.4% |
| Sample. 5G | 1.68 | 1.73 | 1.81 | 1.77 | 1.77 | 0.0900 | 5.4% |

TABLE 38

Physical characteristics of pilling treats

| | Water Activity | Moisture content | Material Cling on Pill: one side exposure (% Pill weight gain) | Adhesive strength | texture |
|---|---|---|---|---|---|
| Vet IQ Pilling Treat | 0.337 | 17% max | 0.00% | 12 g | firm treat dough |
| Pill Pocket Duck & Pea flavor | 0.625 | 31% max | 0.00% | 32 g | very soft dough |
| Pill Pocket Hickory Smoke Flavor | 0.627 | 32% max | 0.00% | 32 g | very soft dough |
| Milk Bone Pill Pouch (Chicken) | 0.71 | 30% max | 0.00% | 38 g | very soft dough |

TABLE 38-continued

Physical characteristics of pilling treats

| | Water Activity | Moisture content | Material Cling on Pill: one side exposure (% Pill weight gain) | Adhesive strength | texture |
|---|---|---|---|---|---|
| Vets + Choice Pill Treats (Peanut) | 0.334 | 17% max | 0.00% | 12 g | firm treat dough |
| Sample 2C | 0.79 | 38% | 15.10% | 7.5 g | very soft gel |
| Sample 3C | 0.84 | 39% | 4.30% | 48 g | med-firm gel |
| Sample 5C | 0.81 | 39% | 6.90% | 184 g | med-firm gel |
| Sample. 6C | 0.78 | 35% | 0.90% | 163 g | firm gel |
| Sample. 1D | 0.75 | 36% | 3.10% | 118 g | firm gel |
| Sample. 1E | 0.81 | 35% | 8.90% | 193 g | firm gel |
| Sample 2E | 0.8 | 37% | 12.90% | 7 g | very weak gel: Pourable |
| Sample. 1F | 0.77 | 35% | 5.20% | 93 g | very firm gel |
| Sample. 2F | 0.71 | 33% | 13.30% | 12.5 g | slightly flowable |
| Sample. 3F | 0.78 | 34% | 5.60% | 153 g | firm gel |
| Sample. 4F | 0.77 | 30% | 13.00% | 123 g | soft gel |
| Sample. 5F | 0.8 | 35% | 8.30% | 3 g | very firm gel |
| Sample 1G | 0.79 | 34% | 6.60% | 72 g | med-firm gel |
| Sample. 2G | 0.75 | 32% | 12.40% | 18 g | soft gel |
| Sample. 5G | 0.78 | 35% | 5.40% | 58 g | med-firm gel |

Example 7. Composition of an Inner Portion

An inner portion can comprise the ingredients shown in Table 39.

TABLE 39

| Total | Ingredient | Dry Mix | Slurry | Digest |
|---|---|---|---|---|
| 3.00% | Sweet Rice flour (Waxy Rice) | 8.14% | | |
| 13.00% | Waxy Maize | 35.28% | | |
| 0.00% | Stabilized Rice Bran (Riceland) | 0.00% | | |
| 0.00% | Sweet Potato Powder | 0.00% | | |
| 10.00% | Dried Molasses | 27.14% | | |
| 1.00% | Gelatin | 2.71% | | |
| 2.00% | SD Chicken meat | 5.43% | | |
| 0.25% | AFB Liver Digest Optimizor B21029 | 0.68% | | |
| 4.00% | Dried Rice Syrup 42DE | 10.85% | | |
| 0.00% | Dried Egg Yolk Product | 0.00% | | |
| 0.50% | Salt | 1.36% | | |
| 1.50% | Micro Guard | 4.07% | | |
| 1.50% | AFB 264 Palatant | 4.07% | | |
| 0.10% | NaturOx Plus | 0.27% | | |
| 0.00% | Black Malted Barley | 0.00% | | |
| 0.00% | Poultry Meal | 0.00% | | |
| 0.00% | | 0.00% | | |
| 6.00% | | | 16.67% | |
| 16.00% | Glycerin | | 44.44% | |
| 14.00% | Rice Syrup 64DE | | 38.89% | |
| 1.00% | Simmon's Stabilized Chicken | | | 34.48% |
| 1.00% | Acidified Calcium Sulfate | | | 34.48% |
| 0.90% | Water | | | 31.03% |
| 24.25% | Process Water | | | |
| 100.00% | | 100.00% | 100.00% | 100.00% |
| | | 36.85% | 36.00% | 2.90% |

The present disclosure illustratively described herein suitably may be practiced in the absence of any element or elements, limitation or limitations that are not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the present disclosure claimed. Thus, it should be understood that although the present disclosure has been specifically disclosed by preferred aspects and optional features, modification and variation of the concepts herein disclosed may be resorted to by those skilled in the art, and that such modifications and variations are considered to be within the scope of this invention as defined by the appended claims.

What is claimed is:

1. A device for cutting a food product comprising an inner portion and an outer portion partially surrounding the inner portion, the device comprising:
    a cutting wheel comprising one or more cutting wires strung between an axle and an outer rim of the cutting wheel, wherein the axle is rotatably attached to a frame;
    a motor functionally attached to the cutting wheel, wherein the motor is operable to rotate the cutting wheel about the axle; and
    one or more containers attached to the outer rim of the cutting wheel, wherein each container is operable to deliver a particulate material to the food product at the cutting wire when the cutting wheel rotates about axle;
    wherein each of the one or more cutting wires cuts a food product conveyed through the cutting wheel into cut pieces of the food product when the cutting wheel rotates about the axle, and wherein the particulate material coats the food product and the cut pieces of the food product.

2. The device of claim 1, wherein the food product is an extruded food product or a co-extruded food product comprising an extruded outer portion comprising a center volume at least partially surrounding the inner portion.

3. The device of claim 1, wherein the food product is a dual textured animal treat.

4. The device of claim 3, wherein the inner portion of the dual-textured food product is adhesive.

5. The device of claim 4, wherein the adhesive inner portion of the cut piece is exposed.

6. The device of claim 1, wherein the particulate material is flavor bits, a compatible powder, or a combination thereof.

7. The device of claim 3, wherein the inner portion of the dual-textured food product is adhesive, wherein the adhesive inner portion of the cut piece is exposed, wherein the particulate material is magnesium stearate powder, and wherein delivering the magnesium stearate to the food product at the cutting wire coats the exposed adhesive portion of the cut piece.

8. The device of claim 3, wherein the inner portion of the dual-textured food product is adhesive, wherein the adhesive inner portion of the cut piece is exposed, wherein the particulate material is flavor bits, and wherein delivering the particulate material to the food product at the cutting wire coats the exposed adhesive portion of the cut piece.

9. The device of claim 1, wherein the motor is attached to the frame.

10. The device of claim 1, wherein the food product is conveyed perpendicular to the cutting wheel.

11. The device of claim 1, wherein the motor is functionally attached to the cutting wheel by a belt engaging the cutting wheel and the motor.

12. The device of claim 11, wherein the belt engages the cutting wheel at the outer rim of the cutting wheel.

13. The device of claim 1, wherein the cutting wires are spaced evenly at the outer rim.

14. The device of claim 1, wherein the cutting wires have a diameter of between about 0.1 mm to about 3 mm or less.

15. The device of claim 1, wherein the cutting wires have a diameter of between about 0.1 mm to about 2 mm or less.

16. The device of claim 1, wherein the cutting wheel comprises 6 cutting wires.

17. The device of claim 1, further comprising a chute attached to the frame, wherein the chute is operable to deliver the cut pieces of the food product away from the device.

18. The device of claim 1, further comprising a conveyor belt operable to convey the food product through the cutting wheel, thereby positioning the food product for cutting by the cutting wires.

* * * * *